United States Patent
O'Reilly

(10) Patent No.: US 12,006,297 B2
(45) Date of Patent: Jun. 11, 2024

(54) ANTIBACTERIAL ACTIVITY OF FUNCTIONALIZED DIHYDROPYRIMIDINES

(71) Applicant: WiSys Technology Foundation, Inc., Madison, WI (US)

(72) Inventor: Matthew Charles O'Reilly, Woodbury, MN (US)

( * ) Notice: Subject to any disclaimer, the term of this patent is extended or adjusted under 35 U.S.C. 154(b) by 7 days.

(21) Appl. No.: 17/574,998

(22) Filed: Jan. 13, 2022

(65) Prior Publication Data

US 2022/0220082 A1    Jul. 14, 2022

Related U.S. Application Data

(60) Provisional application No. 63/136,851, filed on Jan. 13, 2021.

(51) Int. Cl.
| | | |
|---|---|---|
| *C07D 239/22* | (2006.01) | |
| *A61P 31/04* | (2006.01) | |
| *C07D 403/04* | (2006.01) | |

(52) U.S. Cl.
CPC .......... *C07D 239/22* (2013.01); *A61P 31/04* (2018.01); *C07D 403/04* (2013.01)

(58) Field of Classification Search
None
See application file for complete search history.

(56) References Cited

PUBLICATIONS

Milcent, Rene, et al. "Synthesis of Ethyl 2-Aminodihydro-5-pyrimidinecarboxylate Derivatives and 3,7-Diethoxycarbonyl-4,6-dihydro-2,4,6,8-tetraaryl-1H-pyrimido[1,2-a]pyrimidines." J. Heterocyclic Chem. (1997), vol. 34, pp. 329-336. (Year: 1997).*

American Chemical Society. Chemical Abstract Service. RN 2801577-35-3. First entered into STN: Aug. 2, 2022. (Year: 2022).*

\* cited by examiner

*Primary Examiner* — John S Kenyon
(74) *Attorney, Agent, or Firm* — Boyle Fredrickson S.C.

(57) ABSTRACT

Emmacin-related substituted dihydropyrimidine compounds demonstrate potency at low concentrations and inhibit Methicillin-resistant *S. aureus* growth. One such compound is:

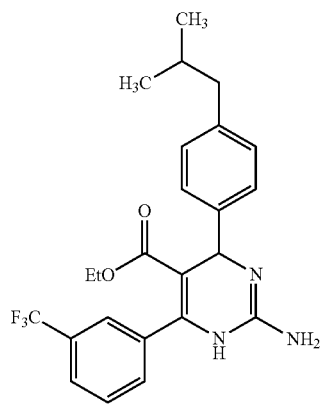

MCO-6-87

Chemical Formula: $C_{24}H_{26}F_3N_3O_2$
Molecular Weight: 445.49

11 Claims, 15 Drawing Sheets

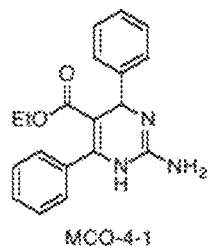
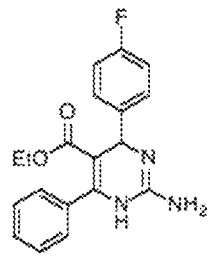
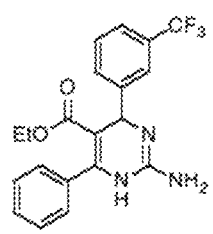

MCO-4-1
Chemical Formula: $C_{19}H_{19}N_3O_2$
Molecular Weight: 321.38

MCO-4-7
Chemical Formula: $C_{19}H_{18}FN_3O_2$
Molecular Weight: 339.37

MCO-4-11
Chemical Formula: $C_{20}H_{18}F_3N_3O_2$
Molecular Weight: 389.38

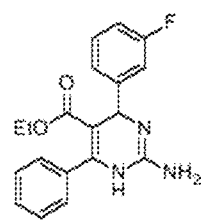
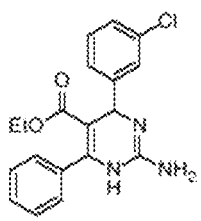
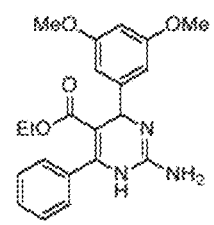

MCO-4-15
Chemical Formula: $C_{19}H_{18}FN_3O_2$
Molecular Weight: 339.37

MCO-4-19
Chemical Formula: $C_{19}H_{18}ClN_3O_2$
Molecular Weight: 355.82

MCO-4-21
Chemical Formula: $C_{21}H_{23}N_3O_4$
Molecular Weight: 381.43

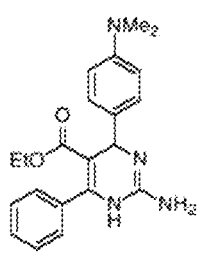
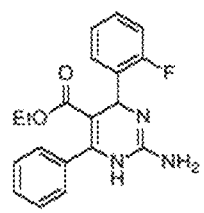
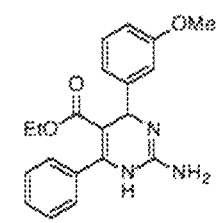

MCO-4-23
Chemical Formula: $C_{21}H_{24}N_4O_2$
Molecular Weight: 364.45

MCO-4-25
Chemical Formula: $C_{19}H_{18}FN_3O_2$
Molecular Weight: 339.37

MCO-4-27
Chemical Formula: $C_{20}H_{21}N_3O_3$
Molecular Weight: 351.41

Figure 5

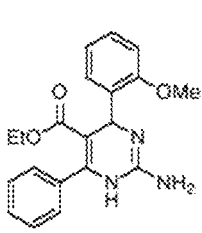

MCO-4-29
Chemical Formula: C₂₀H₂₁N₃O₃
Molecular Weight: 351.41

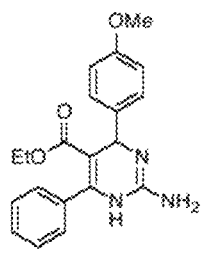

MCO-4-31
Chemical Formula: C₂₀H₂₁N₃O₃
Molecular Weight: 351.41

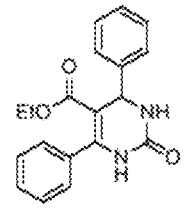

MCO-4-33
Chemical Formula: C₁₉H₁₈N₂O₃
Molecular Weight: 322.36

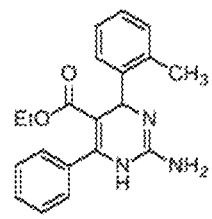

MCO-6-1
Chemical Formula: C₂₀H₂₁N₃O₂
Molecular Weight: 335.41

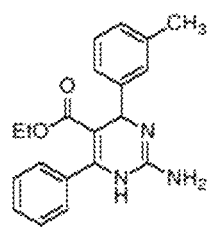

MCO-6-7
Chemical Formula: C₂₀H₂₁N₃O₂
Molecular Weight: 335.41

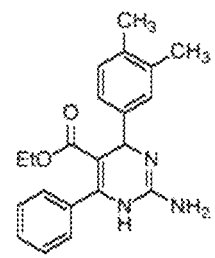

MCO-6-15
Chemical Formula: C₂₁H₂₃N₃O₂
Molecular Weight: 349.43

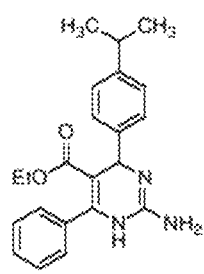

MCO-6-19
Chemical Formula: C₂₂H₂₅N₃O₂
Molecular Weight: 363.46

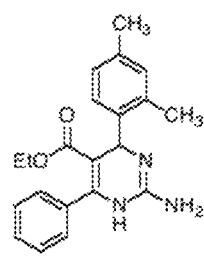

MCO-6-23
Chemical Formula: C₂₁H₂₃N₃O₂
Molecular Weight: 349.43

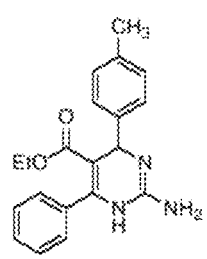

MCO-6-27
Chemical Formula: C₂₀H₂₁N₃O₂
Molecular Weight: 335.41

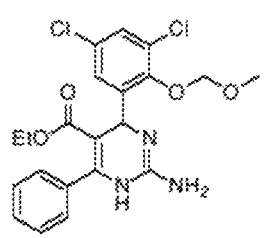

MCO-6-31
Chemical Formula: C₂₁H₂₁Cl₂N₃O₄
Molecular Weight: 450.32

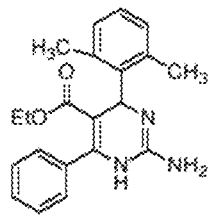

MCO-6-35
Chemical Formula: C₂₁H₂₃N₃O₂
Molecular Weight: 349.43

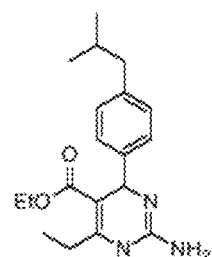

MCO-6-55
Chemical Formula: C₁₉H₂₇N₃O₂
Molecular Weight: 329.44

Figure 5 (cont.)

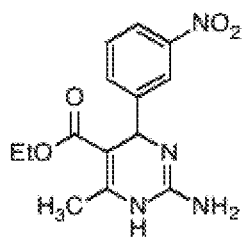

MCO-4-85
Chemical Formula: $C_{14}H_{16}N_4O_4$
Molecular Weight: 304.31

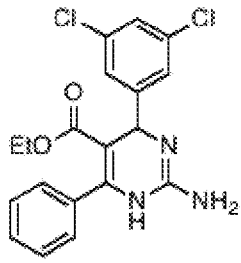

MCO-4-87
Chemical Formula: $C_{19}H_{17}Cl_2N_3O_2$
Molecular Weight: 390.26

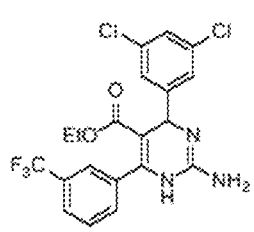

MCO-6-83
Chemical Formula: $C_{20}H_{18}Cl_2F_3N_3O_2$
Molecular Weight: 458.28

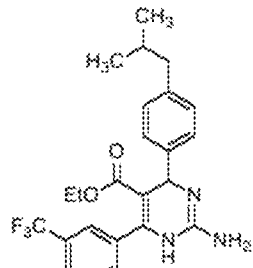

MCO-6-87
Chemical Formula: $C_{24}H_{26}F_3N_3O_2$
Molecular Weight: 445.49

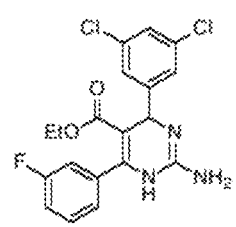

MCO-6-91
Chemical Formula: $C_{19}H_{18}Cl_2FN_3O_2$
Molecular Weight: 408.25

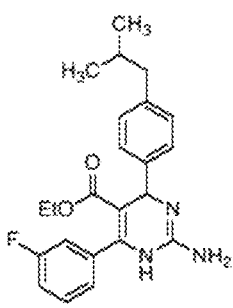

MCO-6-95
Chemical Formula: $C_{23}H_{26}FN_3O_2$
Molecular Weight: 395.48

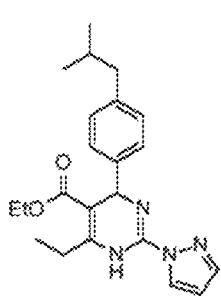

MCO-6-99
Chemical Formula: $C_{22}H_{28}N_4O_2$
Molecular Weight: 380.49

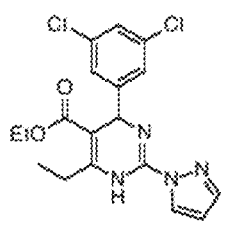

MCO-6-103
Chemical Formula: $C_{19}H_{18}Cl_2N_4O_2$
Molecular Weight: 393.27

Methicillin-Resistant *S. aureus* Minimum Inhibitory Concentrations (MIC) of Commercial Antibiotics (μg/mL)

| Compound | Vancomycin | Gentamicin | Carbenicillin | Erythromycin | Trimethoprim |
|---|---|---|---|---|---|
| ATCC 12600 | 2/S | 4/S | 2/S | <0.5/S | 32/I |
| ATCC 33591 | 2/S | 4/S | 128/S | >512/R | 8/I |
| ATCC 43300 | 2/S | 128/S | 32/S | >512/R | 8/I |

Figure 11

| | USA 300 | | | ATCC 43300 | | | ATCC 12600 | |
|---|---|---|---|---|---|---|---|---|
| Compound | MIC 90 | MIC 50 | Compound | MIC 90 | MIC 50 | Compound | MIC 90 | MIC 50 |
| MCO-4-1 | >64 | 64 | MCO-4-1 | >64 | 64 | MCO-4-1 | >64 | >64 |
| MCO-4-19 | 32 | 16 | MCO-4-19 | 32 | 16 | MCO-4-19 | 32 | 32 |
| MCO-4-49 | 8 | 4 | MCO-4-49 | 4 | 4 | MCO-4-49 | 4 | 4 |
| MCO-VI-10 | 32 | 16_8 | MCO-VI-10 | 32 | 16 | MCO-VI-10 | 16 | 8 |
| MCO-VI-30 | 8 | 4 | MCO-VI-30 | 8 | 4 | MCO-VI-30 | 8 | 4 |
| HAK-1 | 8 | 8 | HAK-1 | 16 | 8 | HAK-1 | 16 | 8 |
| HAK-18 | 32 | 32 | HAK-18 | 32 | 32 | HAK-18 | 32 | 32 |
| HAK-22 | 16 | 8 | HAK-22 | 32 | 16 | HAK-22 | 16 | 8 |
| HAK-36 | 16 | 16 | HAK-36 | 16 | 16 | HAK-36 | 16 | 16 |
| HAK-39 | 16 | 8 | HAK-39 | 16 | 16 | HAK-39 | 16 | 16 |
| HAK-45 | 16 | 8 | HAK-45 | 16 | 8 | HAK-45 | 16 | 8 |
| HAK-46D | 16 | 4 | HAK-46D | 16 | 4 | HAK-46D | 16 | 4 |
| HAK-47 | 32 | 16 | HAK-47 | 32 | 16 | HAK-47 | 32 | 16 |
| HAK-55 | 16 | 8 | HAK-55 | 16 | 8 | HAK-55 | 16 | 8 |
| ZWB-1B | 16 | 8 | ZWB-1B | 16 | 8 | ZWB-1B | 16 | 8 |
| ZWB-2 | 32 | 16 | ZWB-2 | 32 | 32 | ZWB-2 | 32 | 16 |
| ZWB-3C | 64 | 32 | ZWB-3C | 32 | 32 | ZWB-3C | 64 | 32 |
| ZWB-4 | 64 | 32 | ZWB-4 | 64 | 32 | ZWB-4 | 64 | 64 |
| ZWB-5 | 16 | 8 | ZWB-5 | 32 | 16 | ZWB-5 | 32 | 16 |
| ZWB-6 | 32 | 16 | ZWB-6 | 32 | 32 | ZWB-6 | 32 | 32 |
| ZWB-7 | 64 | 32 | ZWB-7 | 64 | 32 | ZWB-7 | 64 | 32 |
| ZWB-8 | 64 | 32 | ZWB-8 | 64 | 64 | ZWB-8 | 64 | 64 |
| ZWB-10 | >64 | 64 | ZWB-10 | >64 | 64 | ZWB-10 | >64 | >64 |
| ZWB-11 | 32 | 16 | ZWB-11 | 32 | 16 | ZWB-11 | 32 | 16 |
| CV-1 | 32 | 16 | CV-1 | 32 | 16 | CV-1 | 32 | 16 |
| CV-7 | >64 | >64 | CV-7 | >64 | >64 | CV-7 | >64 | >64 |
| CV-8 | >64 | >64 | CV-8 | >64 | >64 | CV-8 | >64 | >64 |
| CV-11 | >64 | >64 | CV-11 | >64 | >64 | CV-11 | >64 | >64 |
| CV-12 | >64 | >64 | CV-12 | >64 | >64 | CV-12 | >64 | >64 |
| Erythromycin | 32 | 16 | Erythromycin | >64 | >64 | Erythromycin | 0.5 | 0.5 |
| Carbenicillin | 64 | 64 | Carbenicillin | 32 | 32 | Carbenicillin | 0.5 | 0.5 |
| Gentamycin | 0.5 | 0.5 | Gentamycin | >64 | >64 | Gentamycin | 4 | 2 |
| Trimethoprim | 8 | 4 | Vancomycin | 1 | 1 | Vancomycin | 1 | 1 |
| Vancomycin | 1 | 1 | Trimethoprim | 4 | 4 | Trimethoprim | n/a | 16 |

Figure 13

ANTIBACTERIAL ACTIVITY OF FUNCTIONALIZED DIHYDROPYRIMIDINES

CROSS-REFERENCE TO RELATED APPLICATIONS

This application claims the benefit of U.S. Provisional Patent Application No. 63/136,851, filed Jan. 13, 2021, which is incorporated herein by reference.

STATEMENT REGARDING FEDERALLY FUNDED RESEARCH AND DEVELOPMENT

N/A

FIELD OF THE INVENTION

This invention relates generally to antibiotic resistance. More specifically, this invention relates to functionalized dihydropyrimidine compounds that have an inhibitory effect on the growth of methicillin-resistant S. aureus (MRSA).

BACKGROUND OF THE INVENTION

Infectious disease remains the second leading cause of death worldwide and third in the United States, and these fatalities are largely due to antibiotic resistant bacteria. Antibiotic resistant pathogens are a growing worldwide threat. If left unchecked, deaths due to antibiotic resistant infections could eclipse current cancer mortality rates.

For example, every year in the US, over 2 million people acquire bacterial infections that are resistant to one or more classes of antibiotics and antibiotic resistant (AR) bacteria have been estimated to cost the country as much as 35 billion dollars per year because of various factors including extended hospital stays, costlier interventions, and increased follow-up visits (2008 dollars). Unfortunately, treatment methods often fall short, as AR bacteria take the lives of approximately 35,900 US citizens each year.

Among the AR bacterial threats that the Centers for Disease Control have deemed "serious," methicillin-resistant S. aureus (MRSA) is particularly concerning. MRSA itself causes slightly less than one-third of those overall deaths. MRSA strains are usually resistant to most or all lactam antibiotics (e.g., amoxicillin, methicillin, ampicillin, and penicillin), and many unrelated state-of-the-art antibiotics.

The current emergence and spread of AR bacteria, and specifically, MRSA, combined with the declining discovery of new antibiotics has created a public health crisis.

There are many antibiotics that can be used to treat infections but many of the approved drugs are members of the same class (i.e., structurally similar) and they work through the same mechanisms (i.e., target the same protein/ mechanism). The best method of defense against AR bacteria is the development of new antibiotics that work through secondary mechanisms of action (MOA). The current pace of antibiotic discovery, however, is lower than the rate that bacteria are developing resistance. Further complicating things, industrial efforts toward antibiotic discovery has declined in recent decades, resulting in few approvals.

Specifically, in the 1980s and 1990s, the Food and Drug Administration (FDA) was averaging 2.6 antibiotic approvals per year. From 2000-2017, approvals have dropped 64% to less than 1 per year. Further, newly approved antibiotics often (1) lack novelty (meaning they are simply a derivative of a different approved antibiotic working through the same MOA) and (2) are indicated for very specific infection conditions.

For example, there are at least 18 FDA approved quinolone antibiotics that work through inhibition of topoisomerase, a protein involved in DNA replication. One such quinolone antibiotic is delafloxacin, which was specifically approved for skin infections in 2017. The only other antibiotic approval in 2017 is vabomere, a combination therapy of meropenem (a β-lactam antibiotic approved for use in 1996) and vaborbactam (a novel β-lactamase inhibitor), specifically indicated for urinary tract infections. The β-lactam antibiotic/β-lactamase inhibitor combination is a MOA already comprehensively explored. To keep pace with bacterial resistance, it is critical that antibiotics targeting new or underexploited targets are developed.

One of the most underexploited antibiotic targets is dihydrofolate reductase (DHFR). DHFR is an enzyme that catalyzes the reduction of dihydrofolate to tetrahydrofolate, which is an important cofactor involved in essential cellular processes including the biosynthesis of DNA and amino acids. Therefore, inhibiting DHFR halts cellular growth, which is the basis of its role as a drug target across multiple disease states including antibacterial therapies.

DHFR is inhibited by only one approved antibiotic called trimethoprim (TMP), which was first used in 1962. TMP is an approved antibiotic that targets DHFR, which is an enzyme that reduces dihydrofolate to tetrahydrofolate. Tetrahydrofolate is a cofactor necessary for the biosynthesis of nucleotide bases and amino acids, therefore, treatment with competitive inhibitor TMP blocks enzymatic turnover to halt bacterial growth. While TMP is an effective treatment for many infections, resistance to this antibiotic is increasing, requiring new chemical entities to target DHFR, an underexploited antibiotic target. The only other member of this antibiotic class, Iclaprim, is structurally similar to TMP and works through an identical MOA. TMP is achiral and Iclaprim is administered as the racemate.

It is desirable to have novel DHFR targeting antibiotics, as TMP was released into the clinic in 1962, and resistance was first observed in 1968. Beyond targeting DHFR for antibacterial purposes, inhibition of mammalian DHFR is currently a first-line treatment utilized in the anticancer field using FDA approved pharmaceutical methotrexate, and DHFR inhibition of the malaria parasite by FDA approved pyrimethamine was a mechanism of combating malaria infection that is no longer possible due to widespread resistance. Other laboratories continue to explore DHFR inhibition as an antifungal therapy method.

All three of the FDA approved DHFR inhibitors (trimethoprim, methotrexate, and pyrimethamine) share an aminopyrimidine ring that underlies their common competitive mode of DHFR inhibition. That ring plunges into the DHFR active site in place of the substrate dihydrofolate's pyrimidine ring, which allows for competitive DHFR inhibition. This structural component being identical across molecules directed toward bacteria, mammals, and parasites means that off-target binding could be a concern. In some therapeutic scenarios, the off-target binding is unimportant. For instance, if methotrexate impacts a patient's microbiome while effectively inhibiting the progression of cancer, that impact on the bacteria could be considered mild side effect of the treatment. However, it would be unacceptable for an antibiotic to cause toxicity via off-target inhibition of mammalian DHFR. The latter scenario is likely a partial cause of the lack of DHFR-targeting antibiotics beyond TMP. Iclaprim, the competitive DHFR inhibitor also sharing the common aminopyrimidine ring, has shown non-inferiority (the burden of approval for antibiotics) to vancomycin for the control of skin infections in phase 2 and 3 clinical trials. However, mild to moderate side effects have compelled the FDA to require additional testing prior to approval. TMP and Iclaprim exert their biological effect through competitive DHFR inhibition and because of their similar structures and MOA, bacteria can develop resistance to both antibiotics in an analogous fashion.

This large societal and monetary cost associated with AR bacteria drives a need for continued research and development to combat these infections. Accordingly, there is a long felt need in the medical field for more effective therapeutic compounds and more diverse methods of therapy in this area.

SUMMARY OF THE INVENTION

Here, the inventors demonstrate novel functionalized substituted dihydropyrimidine compounds that have an inhibitory effect on the growth of methicillin-resistant *S. aureus* (MRSA). In certain embodiments, the compound has the structure of any one of the following compounds.

MCO-4-1

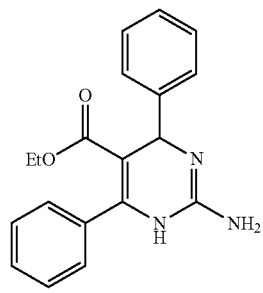

Chemical Formula: $C_{19}H_{19}N_3O_2$
Molecular Weight: 321.38

MCO-4-7

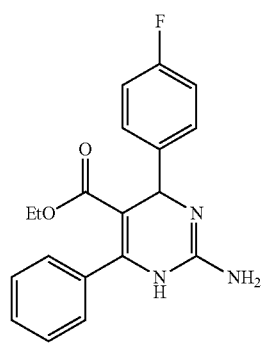

Chemical Formula: $C_{19}H_{18}FN_3O_2$
Molecular Weight: 339.37

MCO-4-11

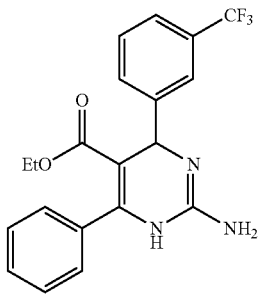

Chemical Formula: $C_{20}H_{18}F_3N_3O_2$
Molecular Weight: 389.38

MCO-4-15

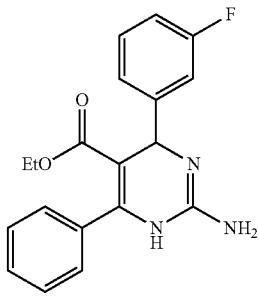

Chemical Formula: $C_{19}H_{18}FN_3O_2$
Molecular Weight: 339.37

MCO-4-19

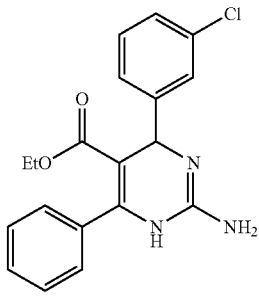

Chemical Formula: $C_{19}H_{18}ClN_3O_2$
Molecular Weight: 355.82

MCO-4-21

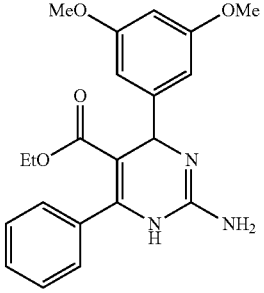

Chemical Formula: $C_{21}H_{23}N_3O_4$
Molecular Weight: 381.43

MCO-4-23

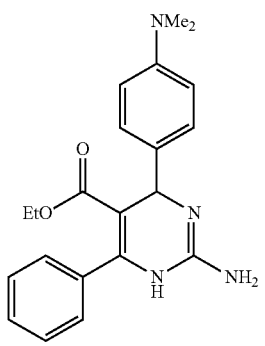

Chemical Formula: $C_{21}H_{24}N_4O_2$
Molecular Weight: 364.45

MCO-4-25

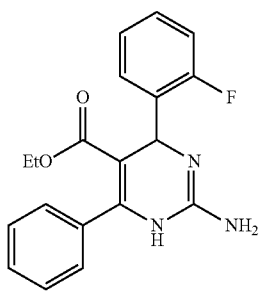

Chemical Formula: $C_{19}H_{18}FN_3O_2$
Molecular Weight: 339.37

MCO-4-27

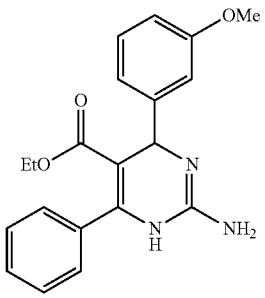

Chemical Formula: $C_{20}H_{21}N_3O_3$
Molecular Weight: 351.41

MCO-4-29

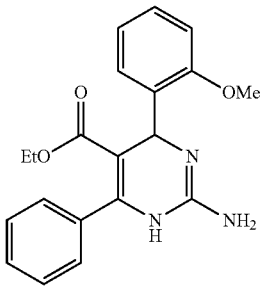

Chemical Formula: $C_{20}H_{21}N_3O_3$
Molecular Weight: 351.41

MCO-4-31

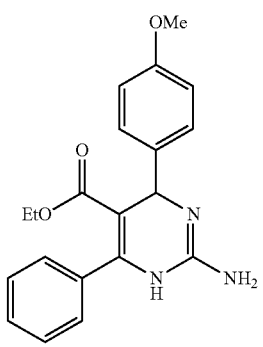

Chemical Formula: $C_{20}H_{21}N_3O_3$
Molecular Weight: 351.41

MCO-4-33

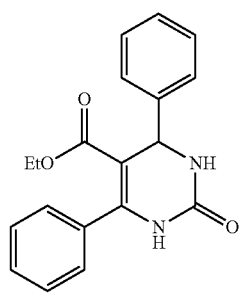

Chemical Formula: $C_{19}H_{18}N_2O_3$
Molecular Weight: 322.36

MCO-6-1

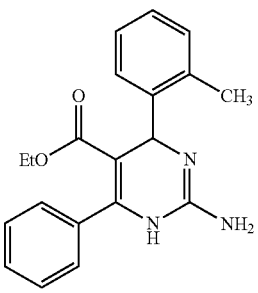

Chemical Formula: $C_{20}H_{21}N_3O_2$
Molecular Weight: 335.41

MCO-6-7

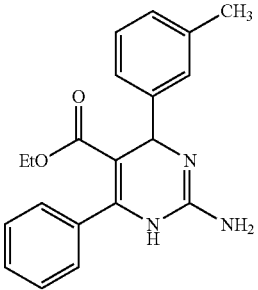

Chemical Formula: $C_{20}H_{21}N_3O_2$
Molecular Weight: 335.41

-continued
MCO-6-15
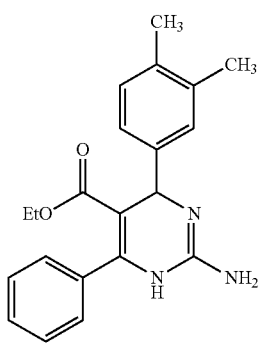
Chemical Formula: $C_{21}H_{23}N_3O_2$
Molecular Weight: 349.43
MCO-6-19
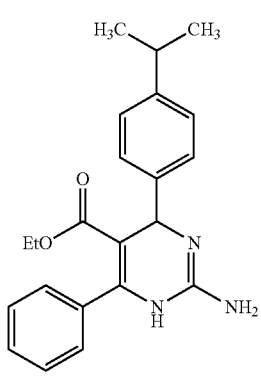
Chemical Formula: $C_{22}H_{25}N_3O_2$
Molecular Weight: 363.46
MCO-6-23
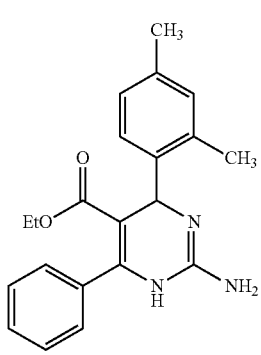
Chemical Formula: $C_{21}H_{23}N_3O_2$
Molecular Weight: 349.43
-continued
MCO-6-27
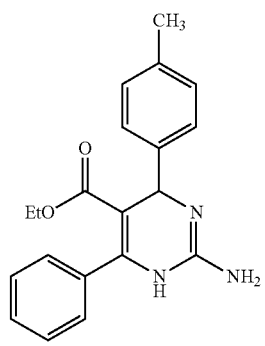
Chemical Formula: $C_{20}H_{21}N_3O_2$
Molecular Weight: 335.41
MCO-6-31
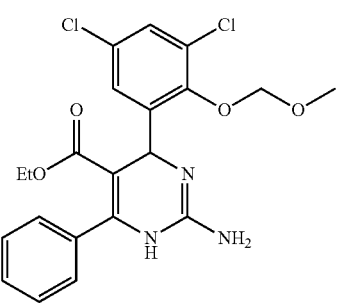
Chemical Formula: $C_{21}H_{21}Cl_2N_3O_4$
Molecular Weight: 450.32
MCO-6-35
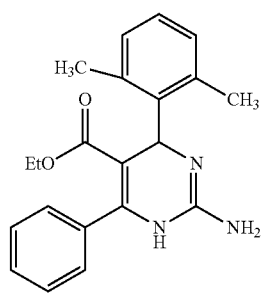
Chemical Formula: $C_{21}H_{23}N_3O_2$
Molecular Weight: 349.43
MCO-6-55
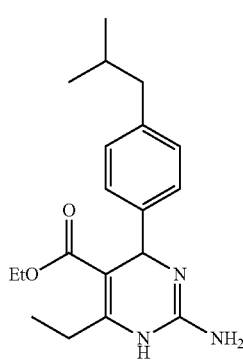
Chemical Formula: $C_{19}H_{27}N_3O_2$
Molecular Weight: 329.44

-continued

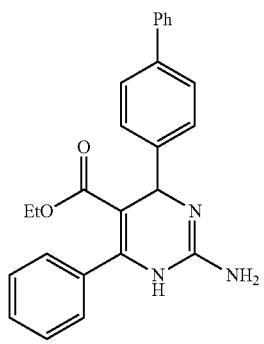

Chemical Formula: C₂₅H₂₃N₃O₂
Molecular Weight: 397.48

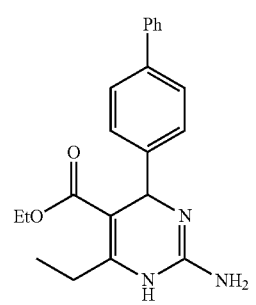

Chemical Formula: C₂₁H₂₃N₃O₂
Molecular Weight: 349.43

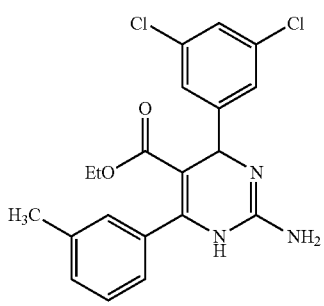

Chemical Formula: C₂₀H₁₉Cl₂N₃O₂
Molecular Weight: 404.29

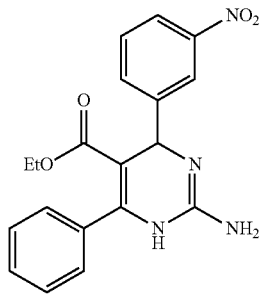

Chemical Formula: C₁₉H₁₈N₄O₄
Molecular Weight: 366.38

-continued

MCO-6-59

MCO-6-63

MCO-6-71

MCO-4-37

MCO-4-43

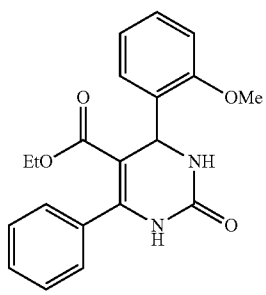

Chemical Formula: C₂₈H₂₀N₂O₄
Molecular Weight: 352.39

MCO-4-45

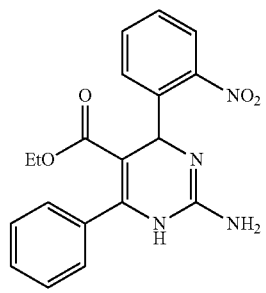

Chemical Formula: C₁₉H₁₈N₄O₄
Molecular Weight: 366.38

MCO-4-47

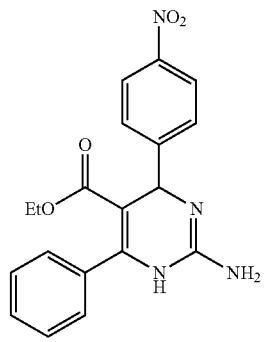

Chemical Formula: C₁₉H₁₈N₄O₄
Molecular Weight: 366.38

MCO-4-49

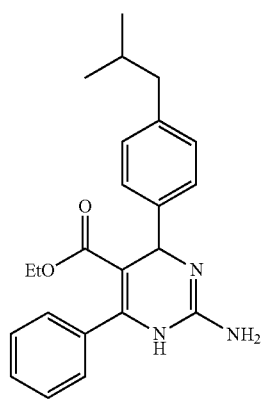

Chemical Formula: C₂₃H₂₇N₃O₂
Molecular Weight: 377.49

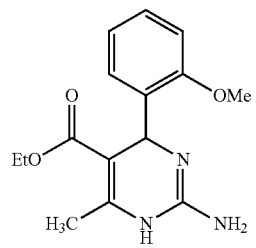

MCO-4-65

Chemical Formula: C₁₅H₁₉N₃O₃
Molecular Weight: 289.34

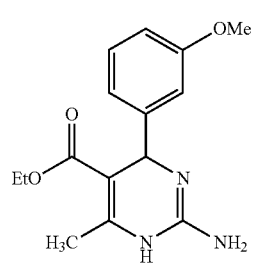

MCO-4-75

Chemical Formula: C₁₅H₁₉N₃O₃
Molecular Weight: 289.34

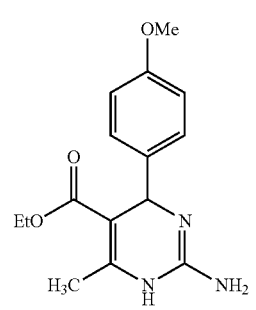

MCO-4-77

Chemical Formula: C₁₅H₁₉N₃O₃
Molecular Weight: 289.34

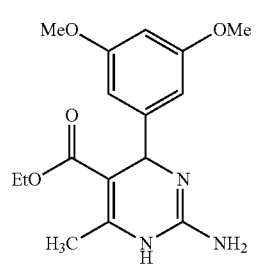

MCO-4-83

Chemical Formula: C₁₅H₂₁N₃O₄
Molecular Weight: 319.36

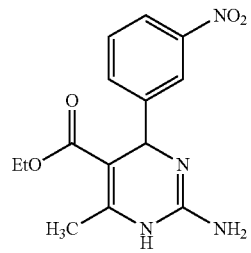

MCO-4-85

Chemical Formula: C₁₄H₁₆N₄O₄
Molecular Weight: 304.31

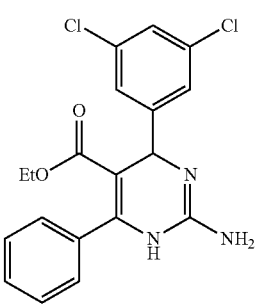

MCO-4-87

Chemical Formula: C₁₉H₁₇Cl₂N₃O₂
Molecular Weight: 390.26

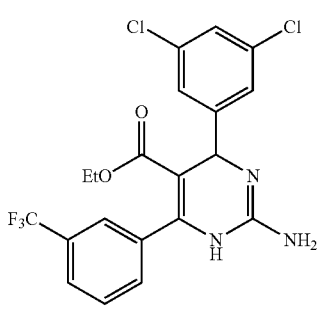

MCO-6-83

Chemical Formula: C₂₀H₁₆Cl₂F₃N₃O₂
Molecular Weight: 458.26

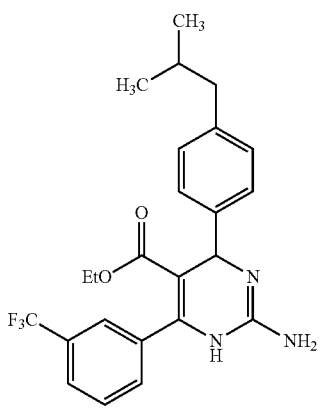

MCO-6-87

Chemical Formula: C₂₄H₂₆F₃N₃O₂
Molecular Weight: 445.49

-continued
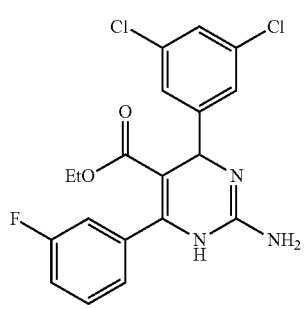
MCO-6-91
Chemical Formula: $C_{19}H_{16}Cl_2FN_3O_2$
Molecular Weight: 408.25
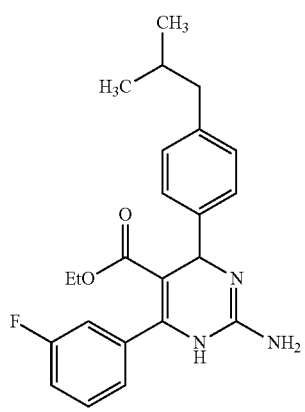
MCO-6-95
Chemical Formula: $C_{23}H_{26}FN_3O_2$
Molecular Weight: 395.48
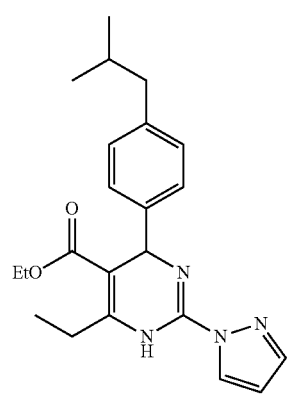
MCO-6-99
Chemical Formula: $C_{22}H_{28}N_4O_2$
Molecular Weight: 380.49
-continued
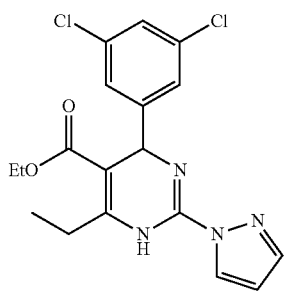
MCO-6-103
Chemical Formula: $C_{18}H_{18}Cl_2N_4O_2$
Molecular Weight: 393.27
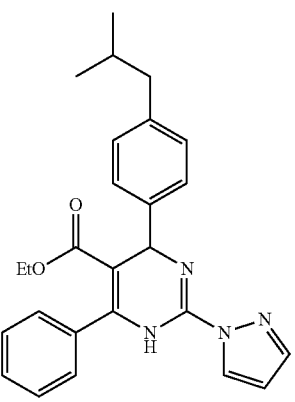
MCO-6-113
Chemical Formula: $C_{26}H_{23}N_4O_2$
Molecular Weight: 428.54
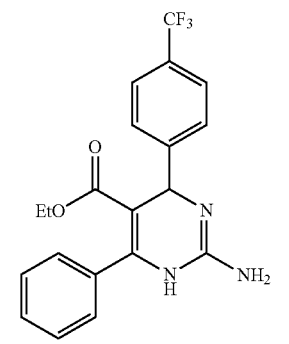
MCO-6-115
Chemical Formula: $C_{20}H_{18}F_3N_3O_2$
Molecular Weight: 389.38
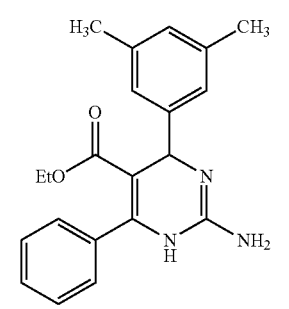
MCO-6-119
Chemical Formula: $C_{21}H_{23}N_3O_2$
Molecular Weight: 349.43

MCO-6-131

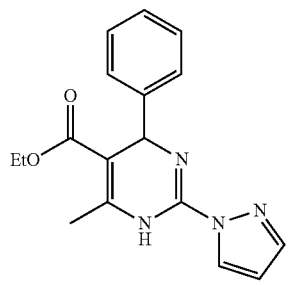

Chemical Formula: C$_{17}$H$_{18}$N$_4$O$_2$
Molecular Weight: 310.36

In alternative embodiments, the compound has the structure of any one of the following compounds.

ZWB-7

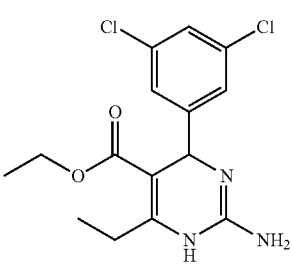

5.6 mg

HAK-47

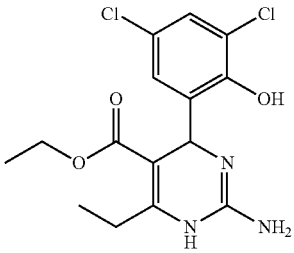



MCO-6-131

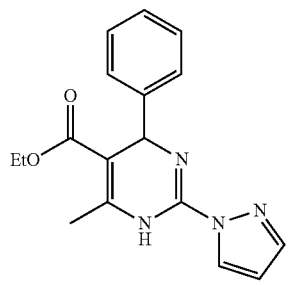

Chemical Formula: C$_{17}$H$_{18}$N$_4$O$_2$
Molecular Weight: 310.36

In alternative embodiments, the compound has the structure of any one of the following compounds.

ZWB-7

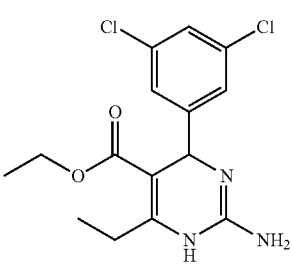

5.6 mg

HAK-47

8.9 mg

MCO-VI-30

6.3 mg

HAK-22

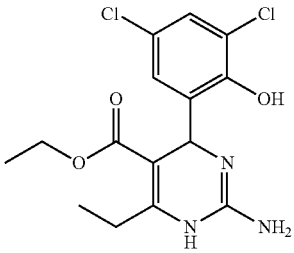

6.7 mg

HAK-46D

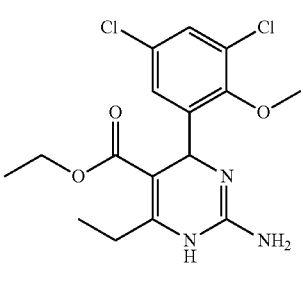

6.4 mg

ZWB-10

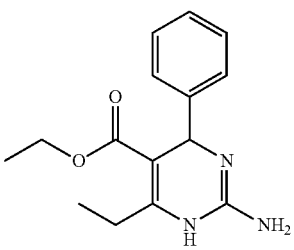

6.4 mg

ZWB-11

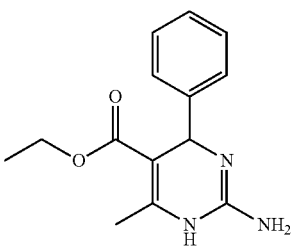

8.0 mg

ZWB-4

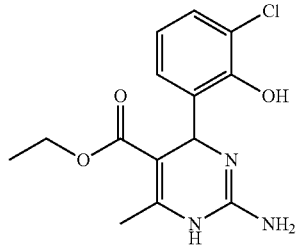

7.2 mg

ZWB-3C
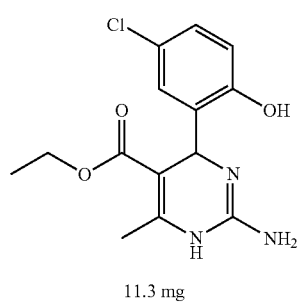
11.3 mg
ZWB-1B
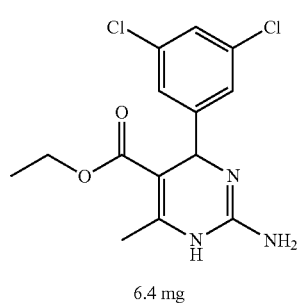
6.4 mg
ZWB-2
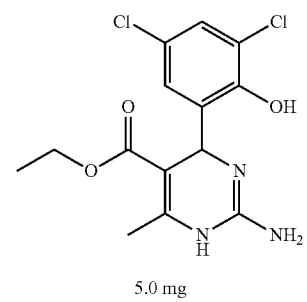
5.0 mg
CV-1
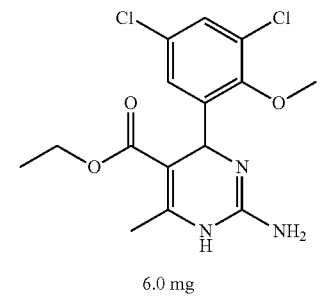
6.0 mg
MCO-4-1
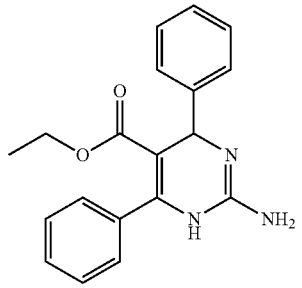
7.8 mg
MCO-4-19
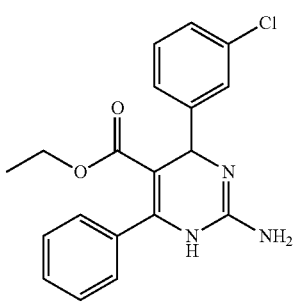
7.7 mg
HAK-36
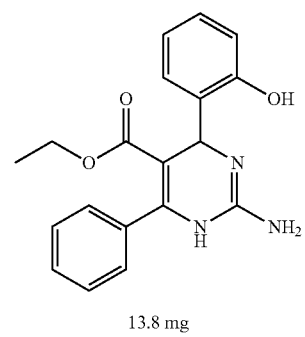
13.8 mg
ZWB-6
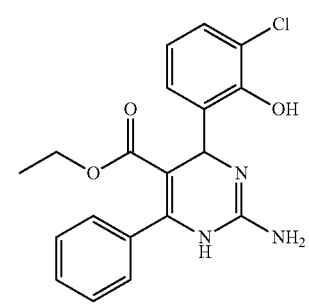
6.7 mg
HAK-1
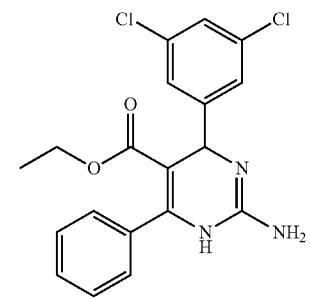
9.0 mg

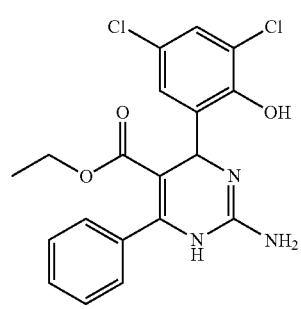
HAK-39
6.4 mg
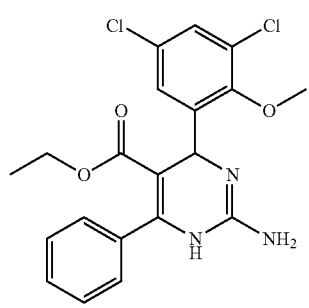
HAK-45
16.3 mg
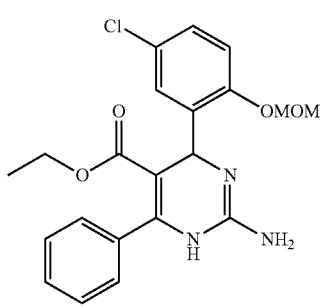
HAK-18
13.0 mg
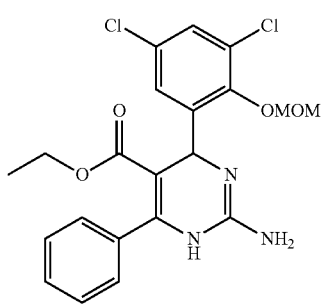
MCO-VI-10
16.1 mg
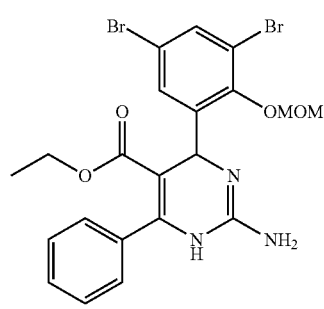
KAH-55
6.3 mg
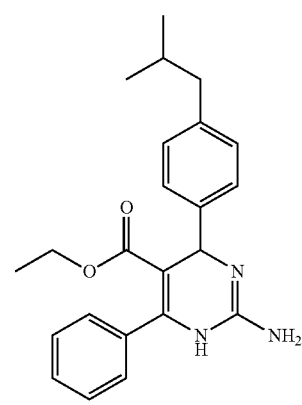
MCO-4-49
8.3 mg
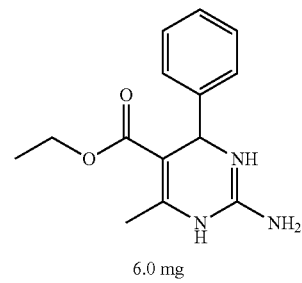
CV-7
6.0 mg
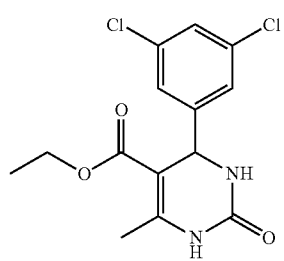
CV-8
6.7 mg

CV-11

6.4 mg

ZWB-8

11.2 mg

CV-12

6.1 mg

The compounds claimed herein may further encompass a pharmaceutically acceptable salt, metabolite, or derivative thereof.

The compounds claimed herein may further demonstrate a minimum inhibitory concentration of at least 2 μg/mL, at least 4 μg/mL, at least 8 μg/mL, or at least 16 μg/mL against Methicillin-resistant *S. aureus* ATCC 33591, Methicillin-resistant *S. aureus* ATCC 43300, and Methicillin-resistant *S. aureus* USA 300. Some compounds are inactive at 64 μg/mL.

Compounds according to the invention may be used to treat a Methicillin-resistant *S. aureus* infection in a subject.

In another aspect of the invention, compounds according to the invention may be used for treating a bacterial infection in a subject.

The present invention further encompasses methods of treating a Methicillin-resistant *S. aureus* infection in a subject, comprising administrating a therapeutically effective amount of the any of the compounds claimed herein, wherein the Methicillin-resistant *S. aureus* infection is treated in the subject.

In another embodiment, the invention includes methods of treating a bacterial infection in a subject, comprising administering an effective amount of the compound claimed herein, wherein the bacterial infection is treated in the subject.

BRIEF DESCRIPTION OF THE DRAWINGS

FIG. 10 is a table illustrating whether the second-generation library of compounds shown in FIGS. 6-9 inhibited the growth of Methicillin Resistant *Staphylococcus aureus*.

FIG. 11 is a table illustrating Methicillin Resistant *Staphylococcus aureus* growth inhibition to selected second-generation library compounds compared to antibiotics.

FIG. 13 is a table illustrating whether the additional series of emmacin-related substituted dihydropyrimidines compounds shown in FIG. 12 inhibited the growth of Methicillin Resistant *Staphylococcus aureus*.

DETAILED DESCRIPTION OF THE INVENTION

Before the present materials and methods are described, it is understood that this invention is not limited to the particular methodology, protocols, materials, and reagents described, as these may vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a", "an", and "the" include plural reference unless the context clearly dictates otherwise. As well, the terms "a" (or "an"), "one or more" and "at least one" can be used interchangeably herein. It is also to be noted that the terms "comprising", "including", and "having" can be used interchangeably.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods and materials are now described.

The disclosed compound formulas and structures can in some cases vary between neutral, acid, and/or basic salt forms, depending on the surrounding environment, and such forms may be used interchangeably herein. As a non-limiting example, a primary amine moiety on a compound may be interchangeably designated as —$NH_2$ or as $NH_3^+$. Furthermore, a given compound may have equivalent resonance structures, which may be used interchangeably herein.

Figure 4:
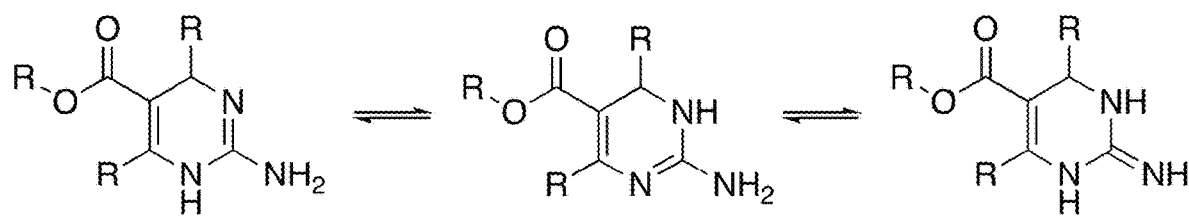
FIG. 4 is chemical schematic of product tautomers of guanidine which exist together in equilibrium.

Referring to FIG. 4, a given compound may have tautomeric structures, which may be used interchangeable herein. As a non-limiting example, guanidine with formula HNC$(NH_2)_2$ exists in equilibrium with multiple versions of the same molecule, all isomeric in nature. The exemplary product tautomers (which can be in equilibrium) are shown.

All publications and patents specifically mentioned herein are incorporated by reference for all purposes including describing and disclosing the chemicals, cell lines, vectors, animals, instruments, statistical analysis and methodologies which are reported in the publications which might be used in connection with the invention. All references cited in this specification are to be taken as indicative of the level of skill in the art. Nothing herein is to be construed as an admission that the invention is not entitled to antedate such disclosure by virtue of prior invention.

As used herein, the term "administering" refers to bringing a subject, tissue, organ or cells in contact with one or more of the emmacin-related substituted dihydropyrimidine compounds described in this disclosure. In certain embodiments, the present invention encompasses administering the compounds useful in the present invention to a patient or subject. A "subject," "patient" and "individual," used equivalently herein, refers to a mammal, preferably a human.

As used herein, the terms "effective amount" and "therapeutically effective amount" refer to the quantity of active therapeutic agents sufficient to yield a desired therapeutic response without undue adverse side effects such as toxicity, irritation, or allergic response. The specific "effective amount" will, obviously, vary with such factors as the particular condition being treated, the physical condition of the patient, the duration of the treatment, the nature of concurrent therapy (if any), and the specific formulations employed.

In this case, an amount would be deemed therapeutically effective if it results in the inhibition of the growth of MRSA. The optimum effective amounts can be readily determined by one of ordinary skill in the art using routine experimentation. Alternatively, an "effective amount" may also include an amount of emmacin-related substituted dihydropyrimidine compound that when Methicillin-resistant *S. aureus* is assayed, the emmacin-related substituted dihydropyrimidine compound provides a minimum inhibitory concentration of at least 16 μg/mL, preferably the emmacin-related substituted dihydropyrimidine compound provides a minimum inhibitory concentration of at least 8 μg/mL, more preferably the emmacin-related substituted dihydropyrimidine compound provides a minimum inhibitory concentration of at least 4 μg/mL, and even more preferably the emmacin-related substituted dihydropyrimidine compound provides a minimum inhibitory concentration of at least 2 μg/mL.

There are few antibiotics left to treat drug resistant bacteria. In some embodiments, compositions of this invention are used to treat infections by drug-resistant strains of bacteria. By "drug-resistant" it is meant that the bacteria are resistant to treatment with one or more conventional antibiotics. To treat AR bacteria such as MRSA, an antibiotic with a different method of action is necessary.

Preliminary studies of dihydropyrimidine derivatives (based on literature compound emmacin) have shown that they can inhibit the growth of MRSA better than many approved antibiotics. Emmacin derivatives leverage an underexploited antibiotic target—dihydrofolate reductase (DHFR)—with a unique noncompetitive mechanism. Emmacin is the only noncompetitive DHFR inhibitor of this class.

To target underexploited DHFR in a novel way, functionalized emmacin-related substituted dihydropyrimidine compounds have been synthesized and examined for their ability to inhibit the growth of MRSA. As the compounds are emmacin derivatives, they likely bind via a unique noncompetitive mechanism and lack mammalian toxicity. The synthesis and biological evaluation of these noncompetitive bacterial DHFR inhibitors as narrow and broad-spectrum antibacterial agents is the focus of this invention.

The disclosure also provides pharmaceutical compositions comprising one or more compounds of this invention in association with a pharmaceutically acceptable carrier. Preferably these compositions are in unit dosage forms such as tablets, pills, capsules, powders, granules, sterile parenteral solutions or suspensions, metered aerosol or liquid sprays, drops, ampoules, auto-injector devices or suppositories; for oral, parenteral, intranasal, sublingual or rectal administration, or for administration by inhalation or insufflation. It is also envisioned that the compounds of the present invention may be incorporated into transdermal patches designed to deliver the appropriate amount of the drug in a continuous fashion.

For preparing solid compositions such as tablets, the principal active ingredient is mixed with a pharmaceutically acceptable carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture for a compound of the present invention, or a pharmaceutically acceptable salt thereof. When referring to these preformulation compositions as homogeneous, it is meant that the active ingredient is dispersed evenly throughout the composition so that the composition may be easily subdivided into equally effective unit dosage forms such as tablets, pills and capsules. The tablets or pills can be coated or otherwise compounded to provide a dosage affording the advantage of prolonged action. For example, the tablet or pill can comprise an inner dosage and an outer dosage component, the latter being in the form of an envelope over the former. The two components can be separated by an enteric layer which, serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the compositions of the present invention may be incorporated for administration orally or by injection include aqueous solutions, suitably flavored syrups, aqueous or oil suspensions, and flavored emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium caboxymethylcellulose, methylcellulose, polyvinylpyrrolidone or gelatin.

The following examples are offered for illustrative purposes only and are not intended to limit the scope of the present invention in any way. Indeed, various modifications of the invention in addition to those shown and described herein will become apparent to those skilled in the art from the foregoing description and the following examples and fall within the scope of the appended claims.

EXAMPLES

Targeting DHFR Allosterically May Provide Greater Inhibitory Selectivity.

While there are significant differences in the catalytic details regarding the dihydrofolate→tetrahydrofolate reaction catalyzed by human (hsDHFR) versus bacterial (ecDHFR) DHFR, the active sites of each enzyme bind tightly to the common aminopyrimidine chemotype present in the FDA approved inhibitors. The differing R-groups connected to the common aminopyrimidine confer the species selectivity of each DHFR inhibitor. In fact, TMP binds to bacterial DHFR 105 times more tightly than mammalian DHFR. DHFR's catalytic activity is maintained across these species despite only 26% sequence agreement (hsDHFR vs ecDHFR). As the active site is functionally conserved across DHFR homologs (no growth could occur without a functional DHFR), the major differences between DHFRs exist beyond the active site. Because of this, it may be possible to more selectively inhibit DHFR if an allosteric ligand was employed, as binding external to the active site may take advantage of DHFR structural elements that are only present in a specific species or group of organisms (i.e. only bacteria).

Further, the development of allosteric inhibitors of any DHFR homolog may represent proof-of-concept applicable to other DHFRs. The synthesis and biological evaluation of allosteric DHFR inhibitor probe molecules as antibacterial agents are the focus of this project. This goal would concurrently produce probe compounds that could be further evaluated as antibiotics with a novel mechanism of action toward a validated antibiotic target, and the unique mechanism may be leveraged toward the design of more selective mammalian or protozoal DHFR inhibitors.

Emmacin Represents A Solid Lead Compound Toward the Development of Allosteric DHFR Inhibitor Probes.

Significant effort toward next generation antibiotics targeting the DHFR enzyme has occurred, but these efforts have focused primarily on competitive inhibition by combining the aminopyrimidine with various R-groups to confer some amount of bacterial selectivity. Very limited effort has occurred toward the development of allosteric DHFR inhibitors.

Emmacin was found to have antibiotic activity, inhibiting the growth of MRSA at concentrations lower than approved antibiotics oxacillin (β-lactam antibiotic) and erythromycin (macrolide antibiotic). Emmacin inhibited DHFR via a unique allosteric uncompetitive mechanism. Emmacin represents a solid lead toward the development of allosteric DHFR inhibitors.

The following examples supports the hypothesis that emmacin derivatives have potent anti-MRSA properties.

Example 1: Preparation of Optically Pure Compounds and Synthesis of Emmacin Analogs Molecules that are nonsuperimposable mirror images are known as enantiomers, and it is widely understood that the biological activity of the racemate (mixture of enantiomers) may be derived from a single enantiomer. Because enantiomers have the same physical properties, they are challenging to prepare in enantiopure form. Because of this, the antimicrobial molecules have only been synthesized as the racemate.

Figure 1:
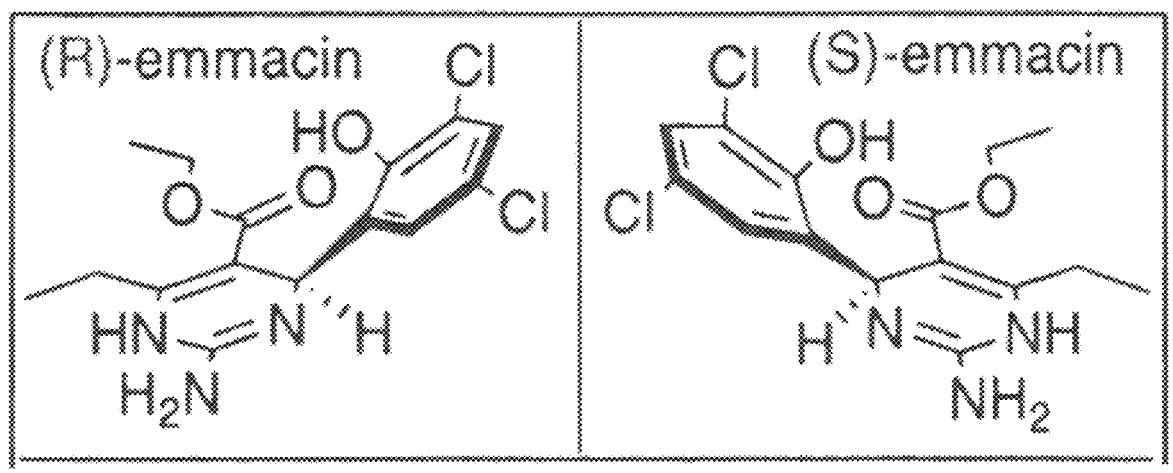
FIG. 1 is a diagram of (R)-emmacin and (S)-emmacin enantiomers of identical physical properties.

Referring now to FIG. 1, because the (R) and (S) enantiomers of the compounds have identical physical properties, it is challenging to isolate them as single enantiomers. To manage this, the present invention involves the synthesis of diastereomeric esters, which will have differing physical properties. They can then be separated by conventional column chromatography.

Figure 2:
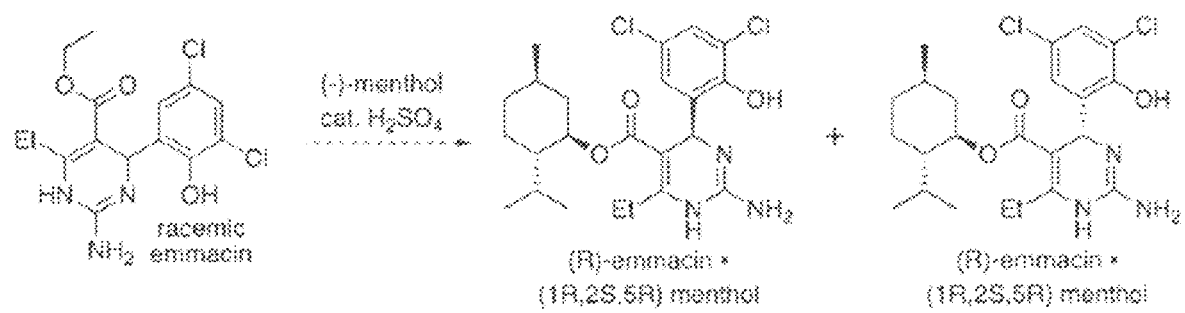
FIG. 2 is a chemical reaction schematic of racemic emmacin with (−)-menthol in catalytic sulfuric acid to promote transesterification and producing a mixture of (R)-emmacin·(1R,2S,5R)-menthol and (S)-emmacin·(1R,2S,5R)-menthol.

Referring now to FIG. 2, racemic emmacin is treated with (−)-menthol in catalytic sulfuric acid to promote transesterification, producing a mixture of (R)-emmacin·(1R,2S,5R)-menthol and (S)-emmacin·(1R,2S,5R)-menthol.

Figure 3:
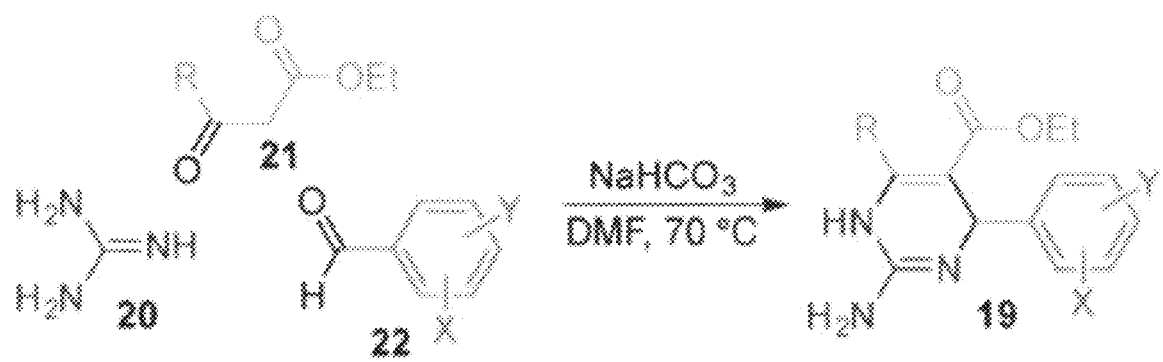
FIG. 3 is a chemical reaction schematic of the synthesis of emmacin analogs via one pot reaction.

Referring now to FIG. 3, an expedient route to synthesize emmacin and structural analogs is as shown. Specifically, a one-pot Biginelli-type reaction can provide emmacin analogs 19 from guanidine 20, β-ketoester 21, and aldehyde 22. The aldehyde and β-ketoester components of this reaction are varied to arrive at emmacin analogs. Further, structural analogs are fashioned through functionalization of emmacin's embedded phenol, amine, and ester groups.

The focused libraries described below in the examples are synthesized and followed with biological screening of these components to determine $MIC_{50}$ values.

Pure DHFR enzymes will also be produced for in vitro screening. Facile expression and purification conditions exist for this enzyme class, and usually involve heterologously expressed polyhistidine-tagged DHFR in E. coli followed by nickel-based affinity chromatography for purification. Once pure DHFR is obtained, kinetics assays can monitor the conversion of dihydrofolate to tetrahydrofolate. The standard assay monitors a loss of absorbance at 340 nm as NADPH is consumed during substrate conversion. Using these assays, $K_m$ and $V_{max}$ values for DHFR can be determined in the presence and absence of the compounds. The inhibitors can be characterized as competitive, noncompetitive, or mixed. Further, $IC_{50}$ values can be determined permitting comparison of phenotypic screening data ($MIC_{50}$ values) with DHFR inhibition.

Example 2: Emmacin-Related Substituted Dihydropyrimidine Compounds and Investigating the Biological Activity of Emmacin-Related Functionalized Dihydropyrimidines Initially, a focused 18-member library of emmacin's 3,5-dichloro-2-hydroxy phenyl ring compounds was designed and synthesized, as shown. The 18-member library of emmacin's 3,5-dichloro-2-hydroxy phenyl ring compounds were investigated to see how individual structural components of emmacin's 3,5-dichloro-2-hydroxy phenyl ring relate to compound activity.

These compounds have been screened at various concentrations (64, 32, 16, and 8 μg/mL) against MRSA (ATCC 33591), and compound 11 prevented bacterial growth at 8 μg/mL. In contrast, FDA approved antibiotics ampicillin, chloramphenicol, and TMP were also included in this compound screen, and none of them were fully able to prevent MRSA growth at concentrations as high as 64 μg/mL.

Figure 5:
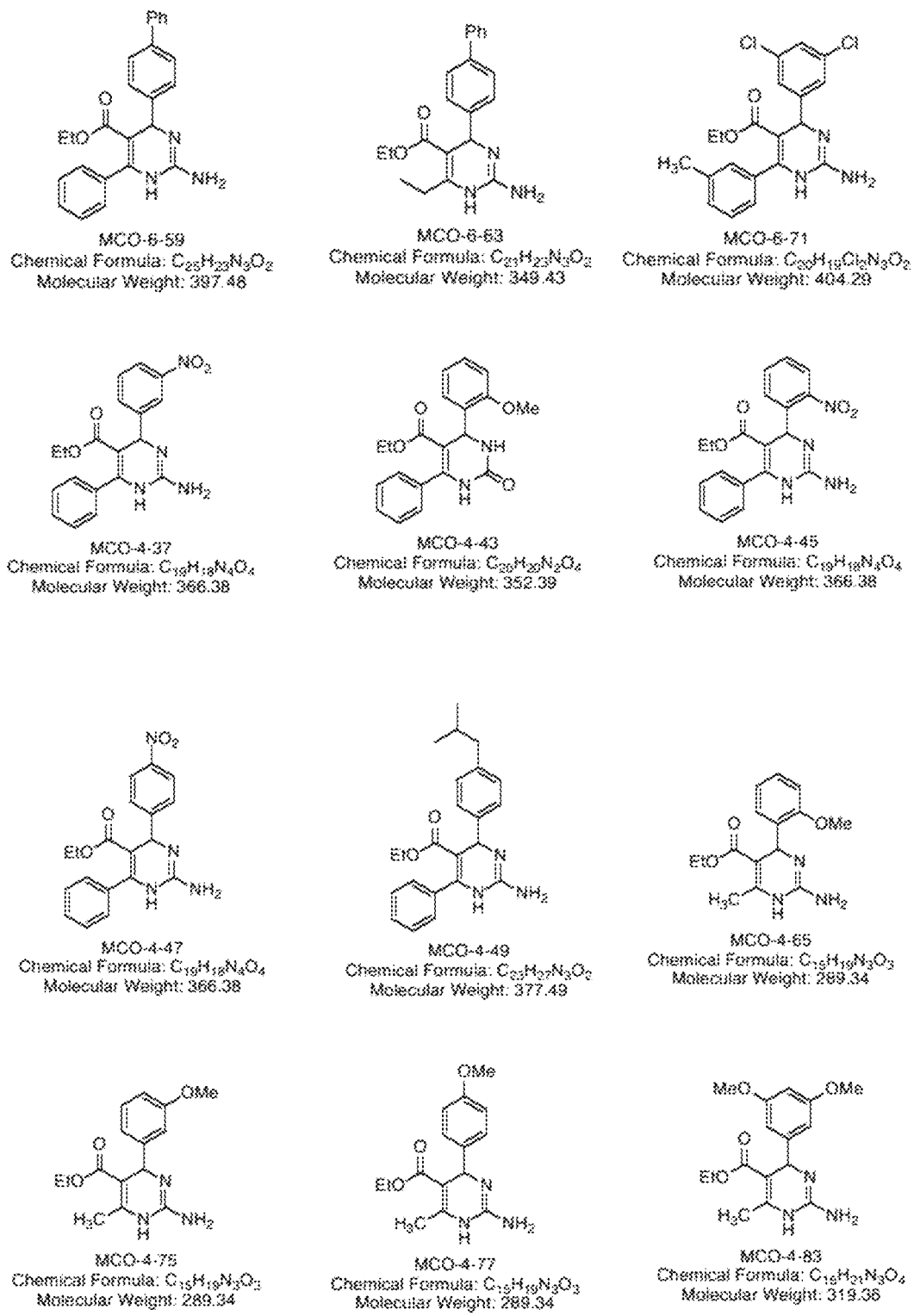
FIG. 5 is a complete series of emmacin-related substituted dihydropyrimidines compounds.
Figure 5:
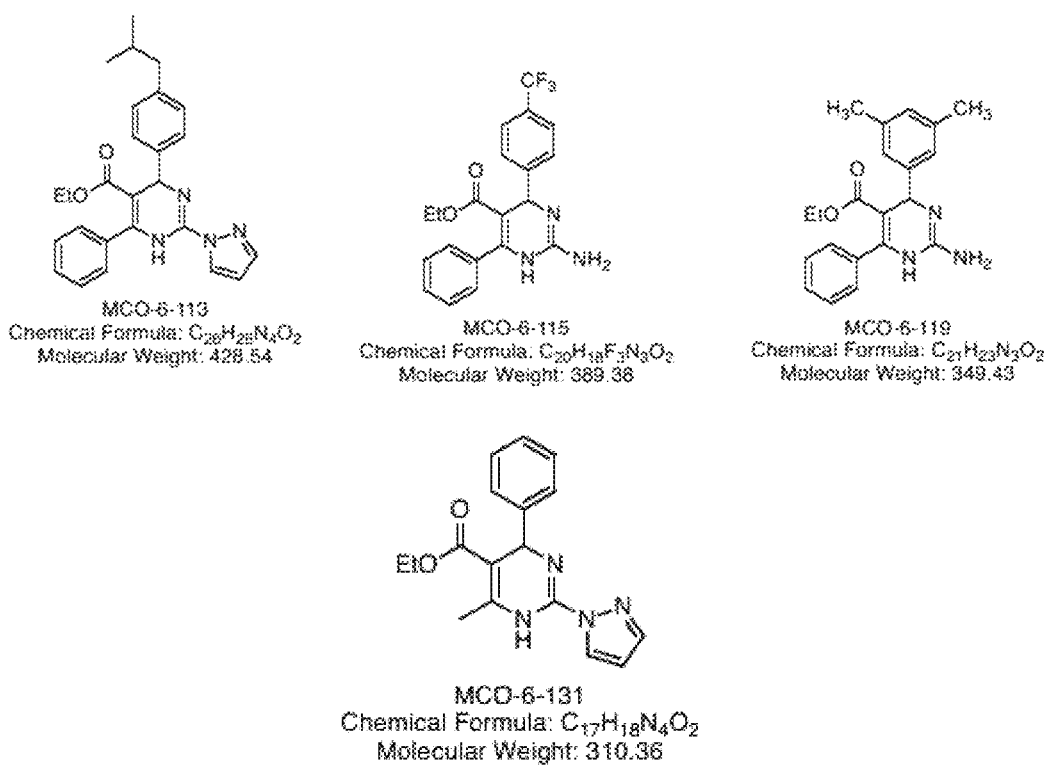

Referring now to FIG. 5, a complete series of 45 emmacin-related substituted dihydropyrimidines compounds may be produced.

These emmacin derivatives demonstrated potency at low concentrations against all three MRSA strains which illustrates a range of activity. More potent molecules from the compound library are shown to be non-inferior to the widely used commercial antibiotics.

Of those compounds, 6-87 was active at 2 µg/mL for all three strains making it a promising molecular structure for DHFR inhibition. 6-87 showed the best inhibition at the lowest concentration with 6-83, 6-59, 6-67, and 6-95 also being promising compounds. 6-87 also demonstrates strong potency against three different MRSA strains compared to some of the commercial antibiotics used to treat MRSA infections that fail to inhibit growth at low concentrations for every strain in our biological assays.

The database of compounds showed potency against *S. aureus* (MRSA) ATCC 43300, *E. coli* ATCC 25922, *A. baumannii* ATCC 19606, and *C. neoformans* CBS 13168. This indicates the broad spectrum of our antibiotics due to their activity against gram-positive bacteria, gram-negative bacteria, and Fungi.

This data shows the ability to create novel compounds in this class with potential for an inhibitory effect on MRSA.

Example 3: First-Generation Compound Library

Figure 6:
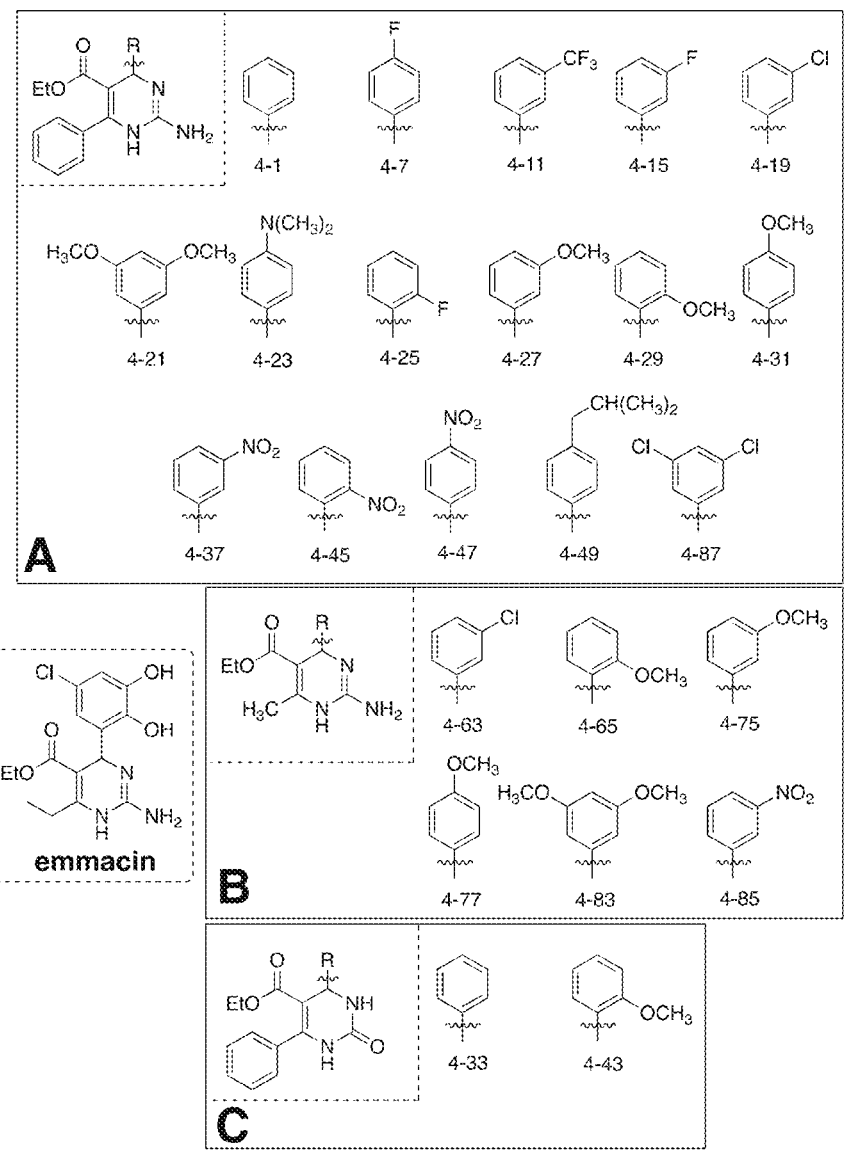
FIG. 6 is a first-generation library of emmacin-related substituted dihydropyrimidines compounds created through modification to the 2-hydroxy-3,5-dichloro arene.

Referring now to FIG. 6, a first generation compound library is created through modification to the 2-hydroxy-3,5-dichloro arene. Installation of varied arene rings in that region were completed via a modified Biginelli reaction, providing various substituents on that ring according to FIG. 6.

The compounds in FIG. 6A have emmacin's ethyl group replaced with a phenyl ring and the 2-hydroxy-3,5-dichloro ring has varied substituents.

FIG. 6B shows the ethyl replaced with a methyl and a variety of methoxy substituted phenyl replacing the 2-hydroxy-3,5-dichloro ring.

FIG. 6C shows replacement of the ethyl group with a phenyl ring, guanidine replacement with a urea, and 2-hydroxy-3,5-dichloro ring replacement with a phenyl and 2-methoxy ring.

Example 4: Second-Generation Compound Library

The most potent compound from the compound library of FIG. 6 was compound 4-49. Compound 4-49 has an isobutyl substituent. Thus, the additional hydrophobic contacts could be what was driving its enhanced activity. Therefore, a second-generation library was created to add hydrophobic substituents to that same ring.

Figure 7:
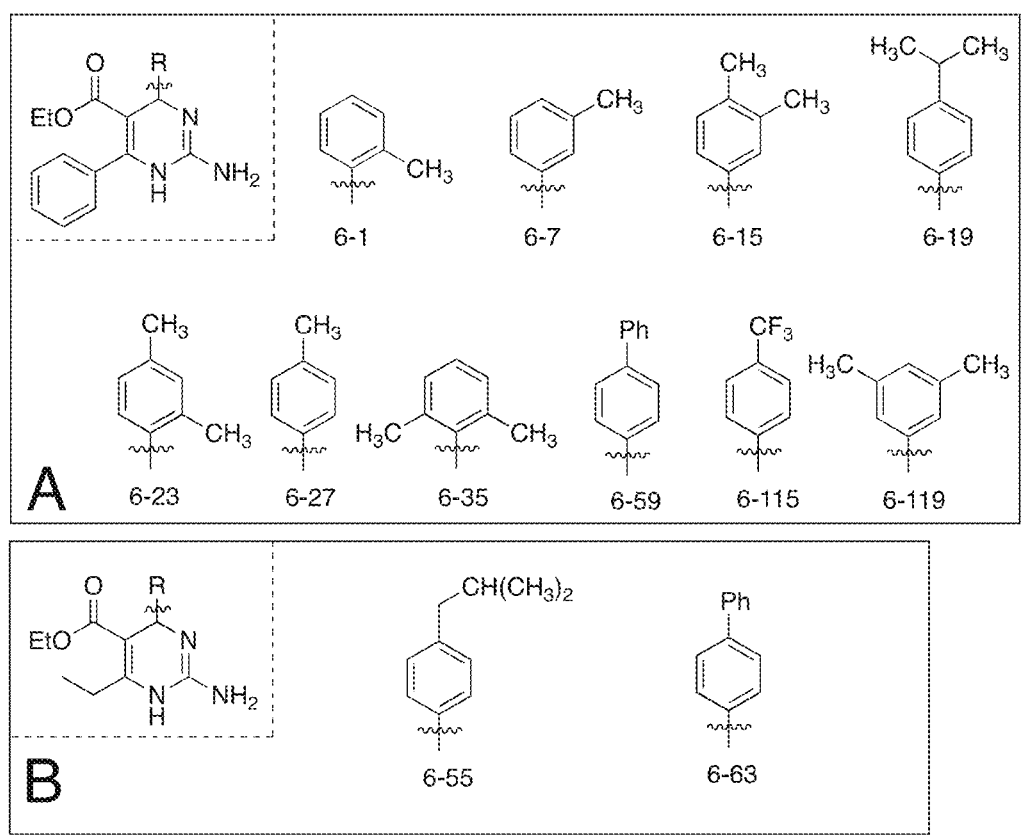
FIG. 7 is a second-generation library of emmacin-related substituted dihydropyrimidines compounds with hydrophobic substituents added to a phenyl ring (FIG. 7A) and a few of the alkyl arene rings combined with the ethyl group (FIG. 7B).

Referring now to FIG. 7, the members of that focused library are shown in FIG. 7A. In order to examine what would occur when emmacin's ethyl group was maintained as an ethyl instead of modified to a phenyl ring, a few of the alkyl arene rings were combined with the ethyl group according to FIG. 7B.

Example 5: Further Phenyl Ring Modifications to the Second-Generation Library

Figure 8:
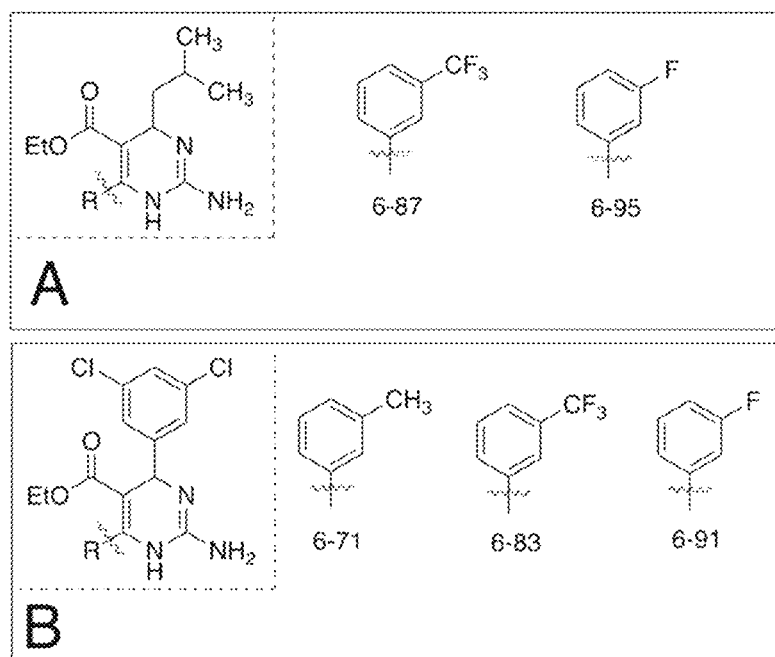
FIG. 8 is a further continuation of the second-generation library of emmacin-related substituted dihydropyrimidines compounds with modifications to the phenyl ring.

Referring now to FIG. 8, additional modifications to the phenyl ring were performed to form the compounds illustrated.

Example 6: Miscellaneous Modifications to the Second-Generation Library

Figure 9:
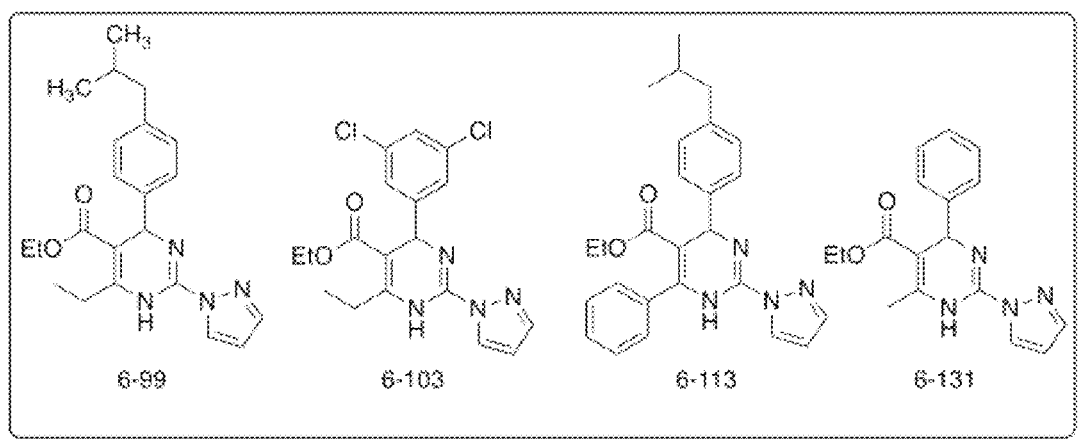
FIG. 9 is a further continuation of the second-generation library of emmacin-related substituted dihydropyrimidines compounds with miscellaneous modifications.

Referring now to FIG. 9, additional miscellaneous modifications were made to form the compounds shown.

Example 7: Antimicrobial Data

Figure 10:
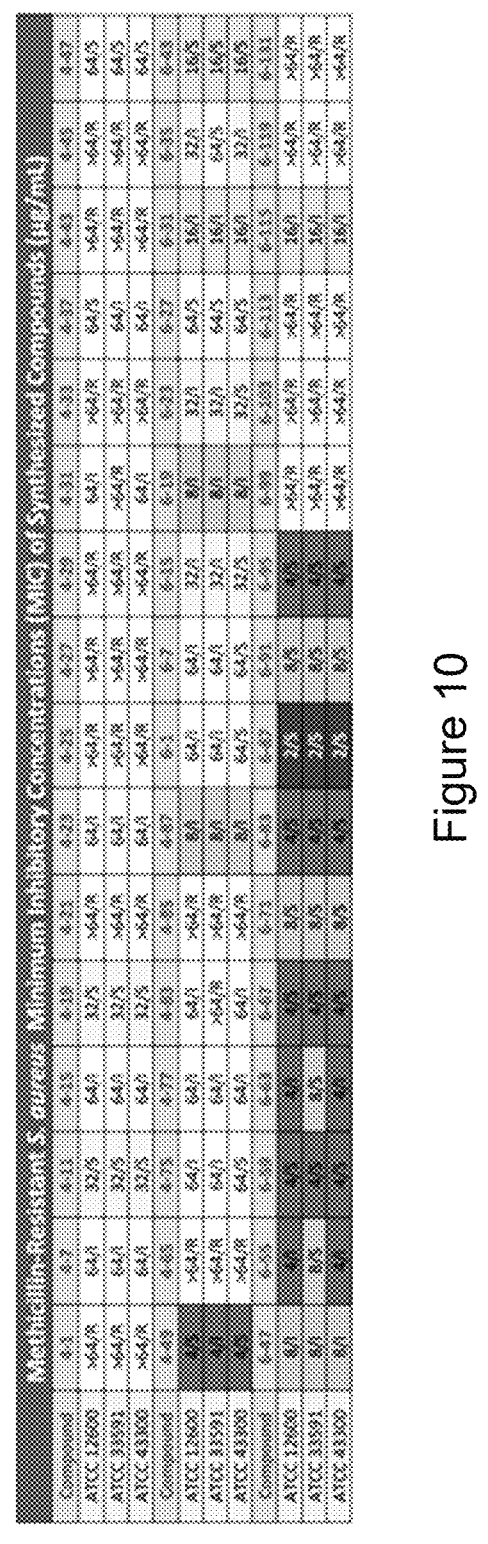

Referring now to FIG. 10, microdilution assays were performed in 96-well plates (in technical duplicates and biological triplicates) to determine if the compounds of Examples 3-6 above inhibited the growth of Methicillin Resistant *Staphylococcus aureus* (growth was determined by reading absorbance at 600 nm using a plate reader) at concentrations ranging from 64 µg/mL to 0.5 µg/mL (1:2 dilutions).

Inhibition was noted by various compounds and others showed no inhibition at any concentrations tested. The minimum inhibitory concentration is noted and it is assigned either an "S" for susceptible, "I" for intermediate, or an "R" for resistant. "S" means bacterial growth is indistinguishable from a negative growth control. "I" means that (1) the concentration was statistically distinct from the positive growth control and (2) bacterial growth was classified as "S" at a higher compound concentration. "R" means inhibition was not noted and the growth was indistinguishable from a positive growth control.

The compounds were examined against three different *S. aureus* strains. ATCC 12600 is methicillin sensitive, and ATCC 33591 and 43300 are both methicillin resistant.

Example 8: Growth Inhibition Compared to Antibiotics

Referring now to FIG. 11, growth inhibition was compared to five antibiotics and the antibiotic susceptibility to the FDA approved antibiotics is indicated in FIG. 10.

It is noteworthy that compound 6-87 inhibits all strains of *S. aureus* at 2 µg/mL, which is indistinguishable from the activity of vancomycin.

Example 9: Additional Emmacin-Related Substituted Dihydropyrimidine Compounds

Figure 12:
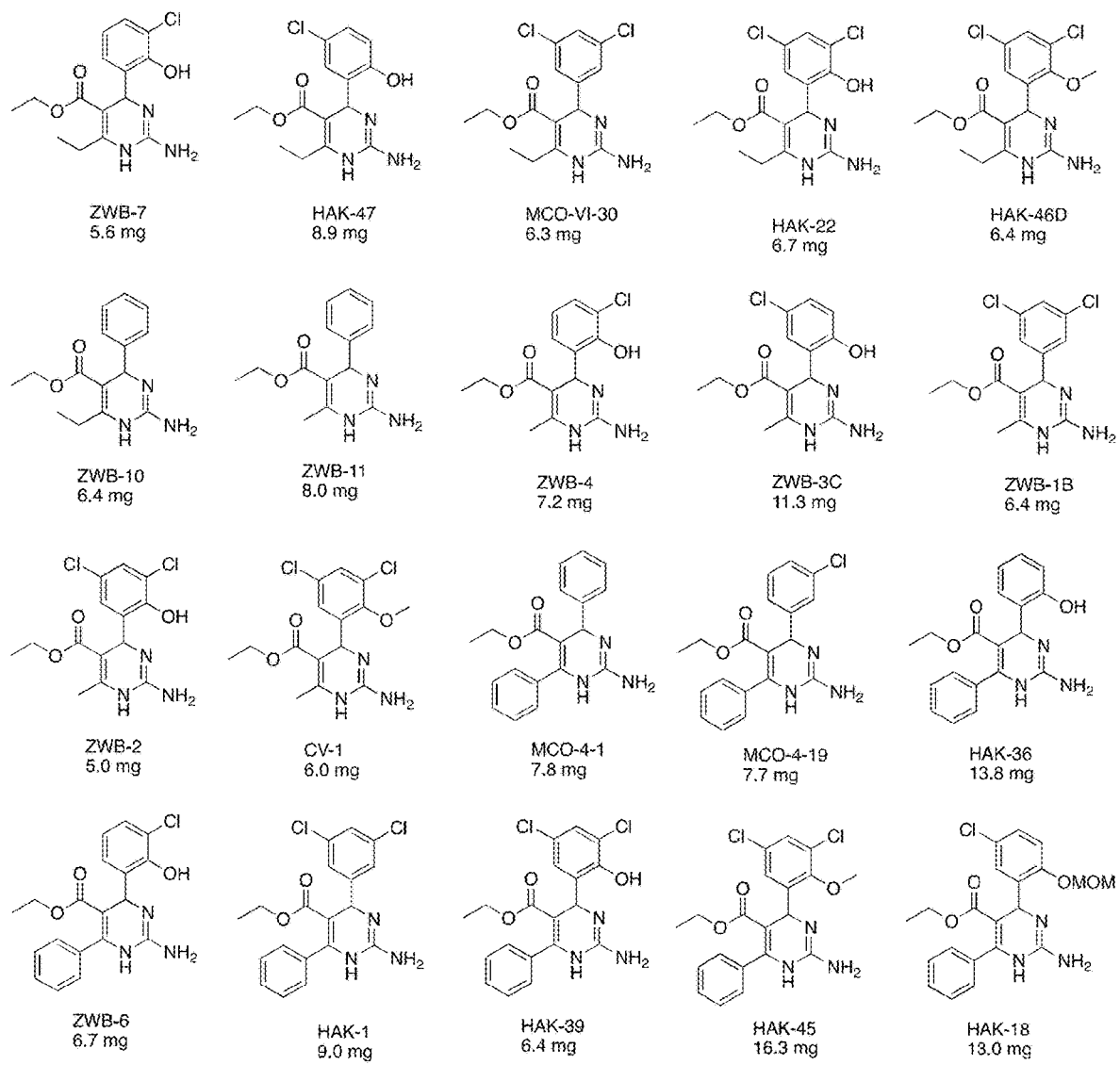
FIG. 12 is an additional series of emmacin-related substituted dihydropyrimidines compounds.
Figure 12:
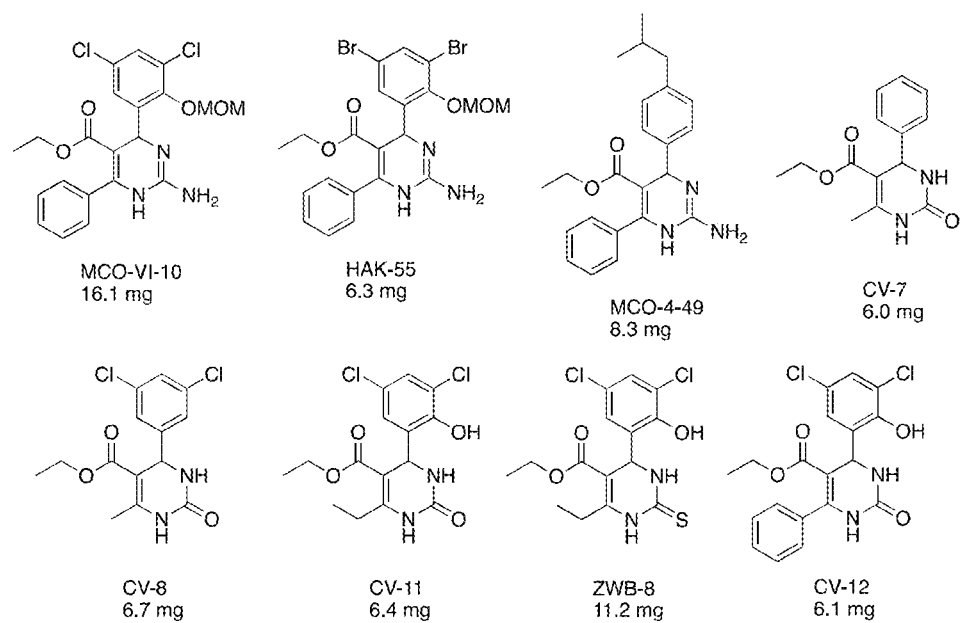

Referring now to FIG. 12, a series of 28 emmacin-related substituted dihydropyrimidines compounds may be produced. These compounds provided greater depth of information related to the SAR of dihydropyrimidines functionalized with an ethyl or methyl group where a phenyl ring existed for much of FIGS. 6 to 9. Most of these compounds have very similarly functionalized arene rings in the "upper" quadrant.

Referring now to FIG. 13, $MIC_{90}$ and $MIC_{50}$ values were determined for the compounds of FIG. 12. In the prior bioactivity table, only $MIC_{90}$ was reported. Specifically, if a number was given alongside an "s", that meant the compound fully inhibited bacterial growth (>90%), versus the letter "i" indicated that the inhibition was present but less than 90%.

FIG. 13 shows $MIC_{90}$ and $MIC_{50}$ data for the compounds. Importantly, this FIG. 13 includes emmacin itself as it was remade as notebook entry HAK-22. HAK-22's $MIC_{90}$ across two MRSA strains and ATCC 12600 was between 32-16 µg/mL, demonstrating the major improvements made upon altering the various R-groups. Most notably, a reasonable number of analogs have activity at the 4 µg/mL level and 6-87 specifically was active as low as 2 µg/mL.

While this invention has been described in conjunction with the various exemplary embodiments outlined above, various alternatives, modifications, variations, improvements and/or substantial equivalents, whether known or that are or may be presently unforeseen, may become apparent to those having at least ordinary skill in the art. Accordingly, the exemplary embodiments according to this invention, as set forth above, are intended to be illustrative, not limiting. Various changes may be made without departing from the spirit and scope of the invention. Therefore, the invention is intended to embrace all known or later-developed alternatives, modifications, variations, improvements, and/or substantial equivalents (including enantiomers) of these exemplary embodiments. All technical publications, patents and published patent applications cited herein are hereby incorporated by reference in their entirety for all purposes.

REFERENCES

1. Aldrich, S. Dihydrofolate Reductase Assay Kit. 2016.
2. Bach, R. D.; Dmitrenko, O. Effect of Geminal Substitution on the Strain Energy of Dioxiranes. Origin of the Low Ring Strain of Dimethyldioxirane. J. Org. Chem. 2002, 67 (ii), 3884-3896.
3. Bett, T. M.; West, F. G. Preparation and Synthetic Applications of Azetidines. *Heterocycles* 2012, 84 (1), 223-264.
4. Benson, S. W.; Cruickshank, F. R.; Golden, D. M.; Haugen, G. It; O'Neal, H. E.; Rodgers, a S.; Shaw, R.; Walsh, R. *Additivity Rules for the Estimation of Thermochemical Properties;* 1969; Vol. 69.
5. Blaskovich, M. A. T.; Zuegg, J.; Elliott, A. G.; Cooper, M. A. Helping Chemists Discover New Antibiotics. *ACS Infect. Dis.* 2016, 1 (7), 285-287.
6. Boucher, H. W.; Talbot, G. H.; Bradley, J. S.; Edwards, J. E.; Gilbert, D.; Rice, L. B.; Scheld, M.; Spellberg, B.; Bartlett, J. Bad Bugs, No Drugs: No ESKAPE! An Update from the Infectious Diseases Society of America. *Clin. Infect. Dis.* 2009, 48 (1), 1-12.
7. Bourne, C. R.; Wakeham, N.; Webb, N.; Nammalwar, B.; Bunce, R. A.; Berlin, K. D.; Barrow, W. W. The Structure and Competitive Substrate Inhibition of Dihydrofolate Reductase from Enterococcus Faecalis Reveal Restrictions to Cofactor Docking. *Biochemistry* 2014, 53 (7), 1228-1238.
8. Bourne, C. IL; Barrow, E. W.; Bunce, IL A.; Bourne, P. C.; Berlin, K. D.; Barrow, W. W. Inhibition of Antibiotic-Resistant *Staphylococcus aureus* by the Broad-Spectrum Dihydrofolate Reductase Inhibitor RABi. *Antimicrob. Agents Chemother.* 2010, 54 (9), 3825-3833.
9. Brandi, A.; Cicchi, S.; Cordero, F. M. Novel Syntheses of Azetidines and Azetidinones. *Chem. Rev.* 2008, 108 (9), 3988-4035.
10. Centers for Disease Control and Prevention (CDC). Antibiotic Resistance Threats in the United States, 2013. *Atlanta CDC* 2013.
11. Chhabra, N.; Aseri, M.; Padmanabhan, D. A Review of Drug Isomerism and Its Significance. *hit. J. Appl. Basic Med. Res.* 2013, 3 (1), 16.
12. Control, C. for D. Infographic: Antibiotic Resistance The Global Threat https://www.cdc.gov/globalhealth/infographics/antibiotic-resistance/antibiotic_resistance-global_threat.htm (accessed Jan. 16, 2017).
13. Dell'Amico, L; Albrecht, L.; Naicker, T.; Poulsen, P. H.; Jorgensen, K. A. Beyond Classical Reactivity Patterns: Shifting from 1,4- to 1,6-Additions in Regio- and Enantioselective Organocatalyzed Vinylogous Reactions of Olefmic Lactones with Enals and 2,4-Dienals. *J. Am. Chem. Soc.* 2013,135, 8063-8070.
14. Donslund, B. S.; Johansen, T. K.; Poulsen, P. H.; Halskov, K. S.; Jorgensen, K. A. The Diarylprolinol Silyl Ethers: Ten Years After. *Angew. Chem. Int. Ed. Engi.* 2015, 54, 2-17.
15. Dowling, M. S.; Fernando, D. P.; Hou, J.; Liu, B.; Smith, A. C. Two Scalable Syntheses of (S)-2-Methylazetidine. *J. Org. Chem.* 2016, 81 (7), 3031-3036.
16. Dudev, T.; Lim, C. Ring Strain Energies from Ab Initio Calculations. *J Am. Chem. Soc.* 1998,120 (18), 44504458.
17. Faigl at al. Novel Stereoselective Synthesis of 1,2,3-Trisubstituted Azetidines. *Tetrahedron Asymmetry* 2012, 23, 1607-1614.
18. Galloway, W. It J. D.; Bender, A.; Welch, M.; Spring, D. R. The Discovery of Antibacterial Agents Using Diversity-Oriented Synthesis. *Chem. Commun.* 2009, No. 18, 2446-2462.
19. Gaunt, M. J.; Johansson, C. C. C.; McNally, A.; Vo, N. T. Enantioselective Organocatalysis. *Drug Discov. Today* 2007, 12 (1-2), 8-27.
20. Gualerzi, C. O.; Brandi, L.; Fabbretti, A.; Pon, C. L. *Antibiotics: Targets, Mechanisms and Resistance;* 2014.
21. Halskov, K. S.; Donslund, B. S.; Paz, B. M.; Jorgensen, K. A. Computational Approach to Diarylprolinol-Silyl Ethers in Aminocatalysis. Acc. Chem. Res. 2016, acs.accounts.6b00008.
22. Jensen, K. L; Dickmeiss, G.; Jiang, H.; Albrecht, L.; Jorgensen, K. A. The Diarylprolinol Silyl Ether System: A General Organocatalyst. *Ace. Chem. Res.* 2012) 45 (2), 248-264.
23. Jiang, H.; Nielsen, J. B.; Nielsen, M.; Jorgensen, K. A. Organocatalysed Asymmetric 3-Amination and Multicomponent Syn-Selective Diamination of A,13-Unsaturated Aldehydes. *Chem.—A Eur. J.* 2007, 13 (32), 9068-9075.
24. Keshipeddy, S.; Reeve, S. M.; Anderson, A. C.; Wright, D. L. Non-Racemic Antifolates Stereo-Selectively Recruit Alternate Cofactors and Overcome Resistance in *S. Aureus. J. Am. Chem. Soc.* 2015, /37, 8983-8990.
25. Lombardo, M. N.; G-Dayanandan, N.; Wright, D. L.; Anderson, A. C. Crystal Structures of Trimethoprim-Resistant DfrAt. Rationalize Potent Inhibition by Propargyl-Linked Antifolates. *ACS Infect. Dis.* 2016, 2, 149-156.
26. Jonathan McConathy, M. J. O. Stereochemistry in Drug Action. *Prim. Care Companion J. Clin. Psychiatry* 2003, 5 (2), 70.
27. Lelais, G.; MacMillan, D. W. C. Modern Strategies in Organic Catalysis: The Advent and Development of Iminium Activation. *Aldrichimica Acta* 2006, 39 (3), 79-87.
28. Morgan, J.; Greenberg, A. Novel Bridgehead Bicyclic Lactams: (A) Molecules Predicted to Have 0-Protonated and N-Protonated Tautomers of Comparable Stability; (B) Hyperstable Lactams and Their 0-Protonated Tautomers. *J. Chem. Thermodyn.* 2014, 73, 206-212.

29. Nammalwar, B.; Bourne, C. R.; Bunce, R. a; Wakeham, N.; Bourne, P. C.; Ramnarayan, K.; Mylvaganam, S.; Berlin, K. D.; Barrow, E. W.; Barrow, W. W. Inhibition of Bacterial Dihydrofolate Reductase by 6-Alkyl-2,4-Diaminopyrimidines. *ChemMedChem* 2012, 7 (11), 1974-1982.

30. Notredame, C.; Higgins, D. G.; Heringa, J. T-Coffee: A Novel Method for Fast and Accurate Multiple Sequence Alignment. *J. Mol. Biol.* 2000, 302 (1), 205-217.

31. O'Connell, K. M. G.; Hodgkinson, J. T.; Sore, H. F.; Welch, M.; Salmond, G. P. C.; Spring, D. R. Combating Multidrug-Resistant Bacteria: Current Strategies for the Discovery of Novel Antibacterials. *Angew. Chemie-Int. Ed.* 2013, 52 (41), 10706-10733.

32. O'Reilly, M. C.; Lindsley, C. W. A General, Enantioselective Synthesis of Protected Morpholines and Piperazines. *Org. Lett.* 2012, 14 (11), 2910-2913.

33. O'Reilly, M. C.; Scott, S. A.; Brown, K. A.; Oguin, T. H.; Thomas, P. G.; Daniels, J. S.; Morrison, R.; Brown, H. A.; Lindsley, C. W. Development of Dual PLD1/2 and PLD2 Selective Inhibitors from a Common 1,3,8-Triazaspiro[4.5]Decane Core: Discovery of ML298 and ML299 That Decrease Invasive Migration in U87-MG Glioblastoma Cells. *J. Med. Chem.* 2013, 56, 2695-2699.

34. Pancholi, A. K.; Geden, J. V.; Clarkson, G. J.; Shipman, M. Asymmetric Synthesis of 2-Substituted Azetidin-3-Ones via Metalated SAMP/RAMP Hydrazones. *J. Org. Chem.* 2016, acs.joc.6b01284.

35. Riehl, J. P. *Mirror-Image Asymmetry*; 2010.

36. Smolinski, M S; Hamburg, M A; Lederberg, J. *Microbial Threats to Health: Emergence, Detection, and Response*; Washington DC: Institute of Medicine, 2003.

37. Spellberg, B.; Guidos, R.; Gilbert, D.; Bradley, J.; Boucher, H. W.; Scheld, W. M.; Bartlett, J. G.; Edwards, J. The Epidemic of Antibiotic-Resistant Infections: A Call to Action for the Medical Community from the Infectious Diseases Society of America. *Clin. Infect. Dis.* 2008, 46(2), 155-164.

38. Wyatt, E. E.; Fergus, S.; Galloway, W. R. J. D.; Bender, A.; Fox, D. J.; Plowright, A. T.; Jessiman, A. S.; Welch, M.; Spring, D. R. Skeletal Diversity Construction via a Branching Synthetic Strategy. *Chem. Commun. (Carob).* 2006, No. 31, 3296-3298.

39. Wyatt, E. E.; Galloway, W. R. J. D.; Thomas, G. L.; Welch, M.; Loiseleur, O.; Plowright, A. T.; Spring, D. R. Identification of an Anti-MRSA Dihydrofolate Reductase Inhibitor from a Diversity-Oriented Synthesis. *Chem. Commun. (Camb).* 2008, 4962-4964.

40. Wyss, P. C.; Gerber, P.; Hartman, P. G.; Locher, H.; Marty, H.; Stahl, M. Novel Dihydrofolate Reductase Inhibitors. Structure-Based versus Diversity-Based Library Design and High-Throughput Synthesis and Screening. *J Med. Chem.* 2003, 46, 2304-2312.

What is claimed is:

1. A compound having the chemical structure of:

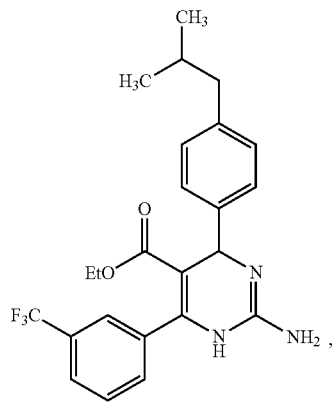 [SMILES: CCOC(=O)C1=C(c2cccc(C(F)(F)F)c2)NC(N)=NC1c1ccc(CC(C)C)cc1]

or a pharmaceutically acceptable salt, metabolite, or derivative thereof.

2. The compound according to claim 1, wherein the compound demonstrates a minimum inhibitory concentration of at least 2 µg/mL against Methicillin-resistant *S. aureus* ATCC 33591.

3. The compound according to claim 2, wherein the compound demonstrates a minimum inhibitory concentration of at least 4 µg/mL against Methicillin-resistant *S. aureus* ATCC 33591.

4. The compound according to claim 3, wherein the compound demonstrates a minimum inhibitory concentration of at least 8 µg/mL against Methicillin-resistant *S. aureus* ATCC 33591.

5. The compound according to claim 4, wherein the compound demonstrates a minimum inhibitory concentration of at least 16 µg/mL against Methicillin-resistant *S. aureus* ATCC 33591.

6. A method of treating a Methicillin-resistant *S. aureus* infection in a subject, comprising administrating an effective amount of the compound according to claim 1, wherein the Methicillin-resistant *S. aureus* infection is treated in the subject.

7. The method according to claim 6, wherein the compound demonstrates a minimum inhibitory concentration of at least 2 µg/mL against Methicillin-resistant *S. aureus* ATCC 33591.

8. The method according to claim 7, wherein the compound demonstrates a minimum inhibitory concentration of at least 4 µg/mL against Methicillin-resistant *S. aureus* ATCC 33591.

9. The method according to claim 8, wherein the compound demonstrates a minimum inhibitory concentration of at least 8 µg/mL against Methicillin-resistant *S. aureus* ATCC 33591.

10. The method according to claim 9, wherein the compound demonstrates a minimum inhibitory concentration of at least 16 µg/mL against Methicillin-resistant *S. aureus* ATCC 33591.

11. A method of treating a bacterial infection in a subject, comprising administering an effective amount of the compound according to claim 1, wherein the bacterial infection is treated in the subject.

* * * * *